US012653679B2

(12) United States Patent
Jongpaiboonkit et al.

(10) Patent No.: US 12,653,679 B2
(45) Date of Patent: Jun. 16, 2026

(54) METHODS AND APPARATUS FOR COATING BONE PARTICLES USING A MESH

(71) Applicant: Warsaw Orthopedic, Inc., Warsaw, IN (US)

(72) Inventors: Leenaporn Jongpaiboonkit, Sterling, MA (US); William J. Bastan, Hillsborough, NJ (US); Timothy Edward Holleran, Howell, NJ (US); Javad A. Mirza, Morganville, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 330 days.

(21) Appl. No.: 17/834,617

(22) Filed: Jun. 7, 2022

(65) Prior Publication Data

US 2023/0390070 A1 Dec. 7, 2023

(51) Int. Cl.
| | |
|---|---|
| *A61F 2/30* | (2006.01) |
| *A61F 2/28* | (2006.01) |
| *A61L 27/56* | (2006.01) |

(52) U.S. Cl.
CPC .... *A61F 2/3094* (2013.01); *A61F 2002/2835* (2013.01); *A61F 2002/30784* (2013.01); *A61F 2002/30971* (2013.01); *A61F 2310/00359* (2013.01); *A61F 2310/00592* (2013.01); *A61L 27/56* (2013.01)

(58) Field of Classification Search
CPC ...................................................... A61L 27/56
See application file for complete search history.

(56) References Cited

U.S. PATENT DOCUMENTS

| | | | |
|---|---|---|---|
| 6,302,913 | B1 | 10/2001 | Ripamonti et al. |
| 6,316,091 | B1 | 11/2001 | Richart et al. |

(Continued)

FOREIGN PATENT DOCUMENTS

| | | |
|---|---|---|
| AU | 2009296439 B2 | 3/2016 |
| AU | 2016226095 | 7/2020 |

(Continued)

OTHER PUBLICATIONS

He, D.; Zhang, X.; Liu, P. Liu, X.; Chen, X.; Ma, F.; Li, W.; Zhang, K.; Zhou, H.; "Effect of Hydrothermal Treatment Temperature on the Hydroxyapatite Coatings Deposited by Electrochemical Method"; Surface & Coating Technology, 2021, vol. 406, p. 1-7.*

(Continued)

*Primary Examiner* — Humera N. Sheikh
*Assistant Examiner* — Julia L Rummel
(74) *Attorney, Agent, or Firm* — Sorell, Lenna & Schmidt, LLP

(57) ABSTRACT

Methods and apparatus for coating bone particles are provided. The methods and apparatus comprise providing a first mesh having a first set of openings to allow coating liquid and bone particles of a select size therethrough and bone particles larger than the select size to remain on the first mesh, the first mesh having a bottom portion; adding bone particles to the first mesh; and contacting the bone particles with coating liquid so as to allow bone particles larger than the first set of openings to remain on the first mesh so as to coat the bone particles.

14 Claims, 9 Drawing Sheets

(56) References Cited

U.S. PATENT DOCUMENTS

| | | | |
|---|---|---|---|
| 7,842,300 B2 | 11/2010 | Atkinson et al. | |
| 8,431,147 B2 | 4/2013 | Drapeau et al. | |
| 8,486,080 B2 | 7/2013 | Mckay | |
| 8,653,029 B2 | 2/2014 | Vickers et al. | |
| 8,926,552 B2 | 1/2015 | Walsh | |
| 8,926,710 B2 | 1/2015 | Mckay | |
| 8,968,323 B2 | 3/2015 | Mckay | |
| 9,034,358 B2 | 5/2015 | Behnam et al. | |
| 9,056,150 B2 | 6/2015 | Gross et al. | |
| 9,308,190 B2 | 4/2016 | Li et al. | |
| 10,772,987 B2 | 9/2020 | Jongpaiboonkit et al. | |
| 2006/0121080 A1* | 6/2006 | Lye | A61L 31/18 |
| | | | 623/1.42 |
| 2006/0251729 A1 | 11/2006 | Kay et al. | |
| 2008/0031914 A1 | 2/2008 | Drapeau et al. | |
| 2009/0177273 A1* | 7/2009 | Piveteau | A61B 17/68 |
| | | | 428/315.7 |
| 2012/0116515 A1 | 5/2012 | Semler et al. | |
| 2012/0310366 A1 | 12/2012 | Li et al. | |
| 2014/0161886 A1 | 6/2014 | Murphy et al. | |
| 2014/0170202 A1 | 6/2014 | Peters et al. | |
| 2014/0209501 A1 | 7/2014 | Govil et al. | |
| 2015/0238655 A1* | 8/2015 | Jongpaiboonkit | |
| | | | A61K 38/1841 |
| | | | 424/602 |
| 2016/0038646 A1 | 2/2016 | Bowlin et al. | |
| 2016/0135954 A1 | 5/2016 | Schlachter et al. | |
| 2016/0166610 A1* | 6/2016 | De Groot-Barrere | A61K 9/14 |
| | | | 424/602 |
| 2016/0271296 A1* | 9/2016 | Jongpaiboonkit | A61L 27/34 |
| 2017/0333190 A1 | 11/2017 | Vickers et al. | |
| 2018/0221539 A1 | 8/2018 | Lehmicke et al. | |
| 2021/0023258 A1* | 1/2021 | Dunkley | A61L 27/46 |
| 2021/0024430 A1* | 1/2021 | Dunkley | C01B 25/32 |
| 2021/0069382 A1 | 3/2021 | Selders et al. | |
| 2025/0121114 A1* | 4/2025 | Pujari-Palmer | C04B 12/02 |

FOREIGN PATENT DOCUMENTS

| | | |
|---|---|---|
| CA | 2978002 | 9/2016 |
| CA | 2740633 C | 2/2019 |
| EP | 3265141 | 1/2018 |
| EP | 2349212 B1 | 1/2022 |
| JP | 2012503673 A | 11/2012 |
| WO | 2010/036919 A1 | 4/2010 |
| WO | 2016005732 A1 | 1/2016 |
| WO | 2016/141242 | 9/2016 |

OTHER PUBLICATIONS

Daculsi, G., et al. "Smart Calcium Phosphate Bioceramic Scaffold for Bone Tissue Engineering," Key Engineering Materials. vols. 529-530: pp. 19-23 (Nov. 29, 2012) (Year: 2012).

Mastergraft Family of Products. webpage. Copyright Umg Uysal Medikal. Website visited Apr. 2022.

Sinha, Sneha, et al. Calcium Phosphate Nanocoatings in Dentistry. European Journal of Molecular & Clinical Medicine, vol. 7, Issue 7, 2020.

Stackable plastic sieves advertised on Amazon.com. webpage. https://www.amazon.com. Website visited Apr. 2022.

Fritsch GmbH. "Fritsch Sieve Shakers." Jan. 6, 2020. Product leaflet. p. 4, 9.

Corca-Huber Debora C et al: "Gentamicin palmitate as a new antibiotic formulation for mixing with bone tissue and local release", Cell and Tissue Banking, Springer, NL, vol. 15, No. 1, Jun. 23, 2013 (Jun. 23, 2013), pp. 139-144.

International Search Report. PCT Appl No. PCT/IB2023/055386. 3 pgs. Nov. 17, 2023.

European Office Action. European Patent Office. Europe Application No. 23 733 441.2-1109. dtd Nov. 26, 2025. 8 pages.

* cited by examiner

| PARAMETERS | IMPROVED COATING PROCESS |
|---|---|
| METHOD | SIEVES SET UP |
| COATING SOLUTION | mSBF |
| COATING CONDITIONS | pH 6.8-7.4, 37°C |
| INCUBATION TIME | 3 DAYS |
| GRANULE SIZE | 90-1600 µm |
| COATING MORPHOLOGY-SEM | LOW MAG: 1,000X<br>HIGH MAG: 10,000X |
| SURFACE AREA-BET | 5.31 -8.83 m²/g (MEAN=6.24) |
| % INCREASED IN SURFACE AREA | 1106%-1840% m²/g (MEAN=1300%) |

BET OF UNCOATED GRANULES = 0.48 m²/g

FIG. 8B

| PARAMETERS | ORIGINAL COATING PROCESS |
|---|---|
| METHOD | ORBITAL/ROTATOR SHAKER |
| COATING SOLUTION | mSBF |
| COATING CONDITIONS | pH 6.8-7.4, 37°C |
| INCUBATION TIME | 4-8 DAYS |
| GRANULE SIZE | 90-1600 µm |
| COATING MORPHOLOGY-SEM | LOW MAG: 1,000X<br>HIGH MAG: 15,000X |
| SURFACE AREA-BET | 0.54 -1.90 m²/g (MEAN=0.84) |
| % INCREASED IN SURFACE AREA | 112%-395% m²/g (MEAN=175) |

BET OF UNCOATED GRANULES = 0.48 m²/g

FIG. 8A

METHODS AND APPARATUS FOR COATING BONE PARTICLES USING A MESH

BACKGROUND

Bone defects or bone voids may be caused by several different factors including, but not limited to, trauma, pathological disease, or surgical intervention. Because bone provides both stability and protection to an organism, these defects or voids can be problematic. To address these defects or voids, compositions that contain natural and synthetic materials have been developed. Bone particles, whether natural bone (e.g., allograft bone) or synthetic bone (e.g., ceramic, polymer) can be used to grow bone in a bone defect. Bone particles may, depending upon the materials contained within them, be used to repair bone and to impart desirable biological and/or mechanical properties to the bone defect.

A variety of bone repair materials and bone void materials are used in the medical field. Autologous cancellous bone is one type of bone void filler used. This type of bone has the advantage of being both osteoinductive and non-immunogenic. Unfortunately, this type of bone is not frequently available. Moreover, donor site morbidity and trauma add to the limitations of autologous cancellous bone.

Allograft bone is a reasonable bone graft substitute for autologous bone. It is readily available from cadavers and avoids the surgical complications and patient morbidity associated with harvesting autologous bone. Allograft bone is essentially a load-bearing matrix comprising cross-linked collagen, hydroxyapatite, and osteoinductive bone morphogenetic proteins (BMPs). Human allograft bone is widely used in orthopedic surgery. However, allograft bone does not always have the same strength properties or the cells and proteins that can influence the growth of new bone like autograft bone provides. Further, when using allograft bone, there is a slight chance of disease transmission and a reduced effectiveness since bone growth cells and proteins are removed during the cleansing and disinfecting process.

An alternative to autograft and allograft bone is synthetic bone material, such as ceramic based bone material. Hybrid materials composed of organic polymers coated with inorganic minerals have attracted much attention in medicine due to their combination of advantageous properties. Polymeric materials are a desirable base material for biomedical applications, as they can be processed into a variety of sizes and geometries and can be designed to bioresorb or bioabsorb in a controllable timeframe. Therefore, polymeric biomaterials have been featured in a variety of applications including medical devices, tissue engineering scaffolds, and drug delivery systems.

Calcium phosphate based mineral coatings represent desirable surfaces for biomedical applications, as they can be similar in composition to bone tissue and have been shown to promote favorable interactions with natural bone, a property known as "bioactivity". The surface modification technology associated with mineral coatings seeks to apply an apatite layer with an engineered nanoparticle sized morphology to the surface of a highly porous biphasic calcium phosphate surface. The mineral coated surface has been demonstrated to stimulate bone cells creating an enhanced cellular environment for bone healing. However, as the surface technology accomplishes bone stimulation through nanoparticle sized morphology features, it is difficult to control the application of nanoparticle sized coatings and increase the coating surface area. The coating of bone particles can often be challenging. For example, when bone particles are in particulate form, the particles can agglomerate or clump, which often leads to an inferior coating.

Sometimes it is desirable to coat bone particles with a nano-coating. Typically, nano coatings have a thickness of 1 nm to less than 1000 nm. Nanocoatings sometimes provide nanostructure to the bone particles, where the surface has particular nano-structures that project from it and can allow the bone to remodel once the bone particles are implanted into the bone defect. Therefore, it would be beneficial to provide methods, apparatus and compositions for coating bone particles.

SUMMARY

Methods and apparatus are provided for coating bone particles with a mineral coating that can be efficiently applied to the bone particles. The methods and apparatus of the current application utilize at least one mesh. Methods and apparatus are also provided for coating bone particles with a nano-coating and/or a nano-coating structure with a particular dimension and geometry (e.g., a plate like morphology) to increase the surface area, which enhances bioactivity of the bone particle and is beneficial in bone remodeling.

In some embodiments, a method of coating bone particles is provided. The method comprises providing a first mesh having a first set of openings to allow coating liquid and bone particles of a select size therethrough and bone particles larger than the select size to remain on the first mesh; adding bone particles to the first mesh; and contacting the bone particles with coating liquid so as to allow bone particles larger than the first set of openings to remain on the first mesh and bone particles smaller than the first set of openings and coating liquid to pass therethrough so as to coat the bone particles.

In some embodiments, an apparatus for coating bone particles is provided. The apparatus comprises a first mesh having a first set of openings configured to allow coating liquid and bone particles of a select size therethrough and bone particles larger than the select size to remain on the first mesh; and a housing or container partially enclosing at least the first mesh, the housing or container having an outlet configured to be fluidly coupled to a pump, the pump configured to provide coating liquid to at least the first mesh to coat the bone particles.

In some embodiments, a porous ceramic granule is provided, the porous ceramic granule comprising hydroxyapatite in an amount of about 8 to about 22 wt. % and beta-tricalcium phosphate in an amount of about 78 to about 92 wt. %. The porous ceramic granule has micropores having an average diameter of about 50 μm to about 800 μm, and each porous ceramic granule having an average particle size of about 0.1 mm to 2.0 mm, the porous ceramic granule having a mineral coating thereon, the mineral coating comprising nanostructures having an average size range from about 5 to about 500 nanometers, wherein the porous ceramic granule has a BET surface area from about 0.4 to about 9.5 m$^2$/g.

While multiple embodiments are disclosed, still other embodiments of the present application will become apparent to those skilled in the art from the following detailed description, which is to be read in connection with the accompanying drawings. As will be apparent, the present disclosure is capable of modifications in various obvious aspects, all without departing from the spirit and scope of the present disclosure. Accordingly, the detailed description is to be regarded as illustrative in nature and not restrictive.

BRIEF DESCRIPTION OF THE DRAWINGS

In part, other aspects, features, benefits, and advantages of the embodiments will be apparent regarding the following description, appended claims and accompanying drawings.

FIG. 8A is an SEM showing the coated bone particles (e.g., granules) using a conventional orbital shaker without the implementation of the methods and apparatus of the present application.

FIG. 8B is an SEM showing the coated bone particles (e.g., granules) coated in accordance with one embodiment of the methods and apparatus of the present application.

Figure 1B:
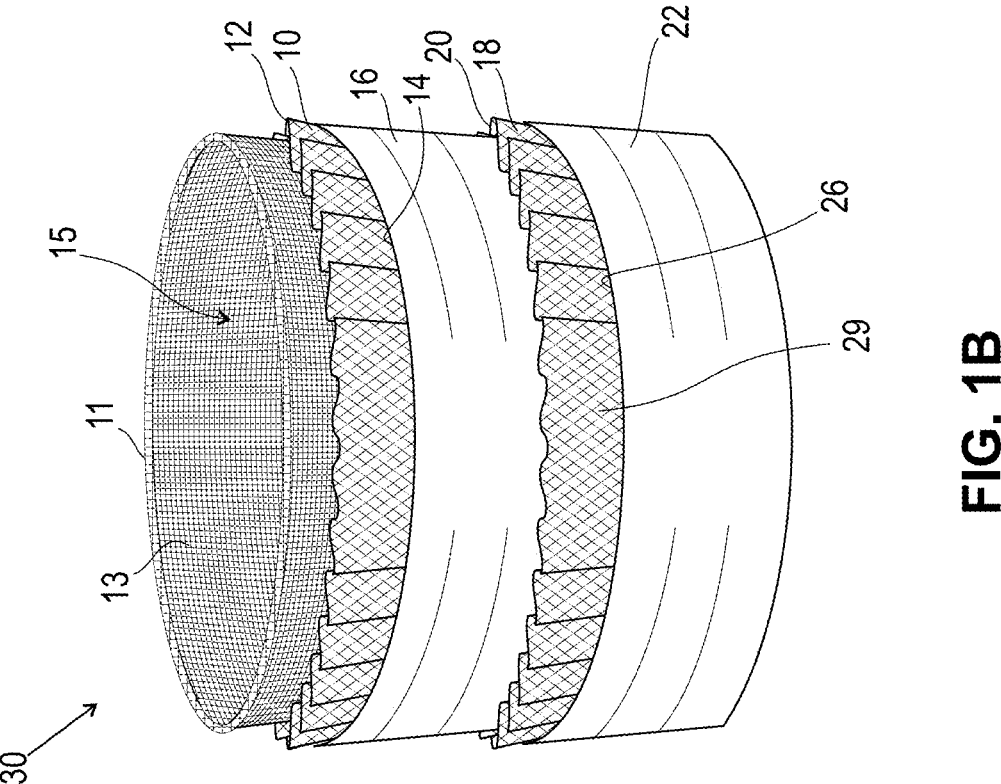
FIG. 1B is a side view of one embodiment of stackable meshes. Here two meshes are shown in a stacked configuration. The first (top) mesh has openings that are larger in size than openings of the second (lower) mesh. The stackable meshes allow bone particles to be coated in a single layer in each individual mesh.

It is to be understood that the figures are not drawn to scale. Further, the relation between objects in a figure may not be to scale and may in fact have a reverse relationship as to size. The figures are intended to bring understanding and clarity to the structure of each object shown, and thus, some features may be exaggerated to illustrate a specific feature of a structure.

DETAILED DESCRIPTION

Definitions

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Similarly, when values are expressed as approximations, by use of the antecedent "about," it will be understood that the particular value forms another embodiment that is +/−10% of the recited value. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value.

Notwithstanding that the numerical ranges and parameters setting forth the broad scope of this application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

"Biocompatible", as used herein, is intended to describe materials that, upon administration in vivo, do not induce undesirable long-term effects.

"Bone", as used herein, refers to bone that is cortical, cancellous, or cortico-cancellous of autogenous, allogenic, xenogenic, or transgenic origin.

"Bone particles" include natural bone or synthetic bone in particulate form or a combination thereof. Bone particles include natural or synthetic granules, fibers, powder, chips, shards, demineralized bone particles, surface demineralized bone particles, ceramic particles, or a combination thereof. Bone particles, whether natural or synthetic can be in any shape including triangular, oval, oblong, spherical, cube shaped, cylindrical shape, or other shapes having regular, irregular or random geometries. The bone particles of the current application can be shaped, lyophilized, molded, hydrated, made flowable, injected, or made into a putty or paste.

The term "autograft" refers to graft material harvested from the same individual patient who is also recipient of the graft, obtained surgically from non-essential donation sites in the patient.

Bone graft, as used herein, refers to any implant prepared in accordance with the embodiments described herein and therefore may include expressions such as a bone void filler.

The terms "macroparticle" or "macroform" include particles that are visible to the naked eye. Typically, the macroparticle can be from 0.01 mm to about 50 mm in length. It will be understood that the terms macroparticle and macroform can be used interchangeably.

The term "nano-sized feature" includes recesses, projections or a combination thereof that are in nanometer size.

The term "osteoinductive," as used herein, refers to the quality of being able to recruit cells from the host that have the potential to stimulate new bone formation. Any material that can induce the formation of ectopic bone in the soft tissue of an animal is considered osteoinductive.

The term "osteoinduction" refers to the ability to stimulate the proliferation and differentiation of pluripotent mesenchymal stem cells (MSCs). In endochondral bone formation, stem cells differentiate into chondroblasts and chondrocytes, laying down a cartilaginous ECM, which subsequently calcifies and is remodeled into lamellar bone. In intramembranous bone formation, the stem cells differentiate directly into osteoblasts, which form bone through direct mechanisms. Osteoinduction can be stimulated by osteogenic growth factors, although some ECM proteins can also drive progenitor cells toward the osteogenic phenotype.

The term "osteogenic" refers to the ability of a graft material to produce bone independently. To have direct osteogenic activity, the graft must contain cellular components that directly induce bone formation. For example, an allograft seeded with activated MSCs would have the potential to induce bone formation directly, without recruitment and activation of host MSC populations. Because many osteoconductive allografts also can bind and deliver bioactive molecules, their osteoinductive potential will be greatly enhanced.

The term "patient" refers to a biological system to which a treatment can be administered. A biological system can include, for example, an individual cell, a set of cells (e.g., a cell culture), an organ, or a tissue. Additionally, the term "patient" can refer to animals including, but not limited to humans, other primates such as chimpanzees, apes, orangutans and monkeys, rats, mice, cats, dogs, cows, horses, etc.

The term "implantable" as used herein refers to a biocompatible device (e.g., the bone particles) retaining potential for successful placement within a mammal. The expression "implantable composition" and expressions of the like as used herein refer to an object implantable through surgery, injection, or other suitable means whose primary function is achieved either through its physical presence or mechanical properties.

The term "moldable" includes that the composition can be shaped by hand or machine or injected into the target tissue site (e.g., bone defect, fracture, or void) into a wide variety of configurations to fit within the bone defect.

The term "cohesive" as used herein means that the composition tends to remain a singular, connected mass upon the addition of fluid, autograft bone or during manipulation, including the exhibition of the ability to be molded or shaped without breaking upon manipulating, or disintegrating or becoming unstable.

The term "flowable" includes that when the bone particles are mixed with a fluid, they can be administered in an injectable state via a syringe and/or cannula. The bone particles can be flowable when its consistency is fluid-like and has a viscosity that is lower than that of the viscosity of the bone particles when in a putty or paste form. Flowable bone particles include liquid or fluid (e.g., solution, suspension, or the like) or semi-solid compositions (e.g., gels, cements) that are easy to manipulate and may be brushed, sprayed, dripped, injected, shaped and/or molded at or near the target tissue site. In various embodiments, the bone particles may be used to fill one or more voids in a bone defect (e.g., an osteolytic lesion).

The term "hydrate," "hydration," "hydratable," "hydrating" or "hydrated" refers to adding an amount of fluid to the bone particles to increase the amount of moisture content in the composition to form a gel, putty or paste that is flowable.

The term "dehydrated" or "dehydration" refers to bone particles that contain a small amount of residual moisture or no moisture content and can be in the form of a dry composition. The dehydrated composition can have a moisture content from about 0 to about 10% based on the total weight of the composition. In some embodiments, when a composition is dehydrated, fluid can be added to the composition to hydrate the composition. A dehydrated composition includes a lyophilized or freeze-dried composition.

The term "bone marrow aspirate" or "BMA" refers to bone marrow fluid that can be obtained via a syringe and needle to harvest the bone marrow fluid from the patient. Bone marrow aspirate comprises fluid that contains a heterogeneous mix of stem and progenitor cells, platelets, and white blood cells. The bone marrow aspirate can be harvested from various sources in the body including, but not limited to, the iliac crest. In some embodiments, the BMA can be used to hydrate the bone particles.

Coating Methods and Apparatus

There is a need for methods and apparatus for coating bone particles with a mineral coating that can be efficiently applied to the bone particles. Methods and apparatus for coating bone particles with a mineral coating that can provide a nano-coating thickness and/or nano-coating structure would also be beneficial. Such methods, while increasing the coated surface area, are capable of being automated and decrease the requirement for manual manipulation of the materials to be coated. There is also a need to produce bone particles having more mineral coating distributed on the bone particle's surface to increase the surface area, which enhances bioactivity of the bone particle and is beneficial in bone remodeling.

Methods and apparatus are provided for coating bone particles with a mineral coating that can be efficiently applied to the bone particles. The methods and apparatus of the current application utilize at least one mesh that can be stacked with one or more meshes. The meshes have a plurality of openings for smaller bone particles and coating liquid to pass therethrough, while larger bone particles that are larger than the openings stay on top of the mesh. Typically, meshes with larger openings are stacked on top of meshes with smaller openings. In this way, bone particles of select sizes can be contacted (e.g., incubated, submerged, suspended, bathed, etc.) with coating liquid. These bone particles can not only have an increased coating surface applied to their surfaces, but the coating application to the bone particles can carefully be controlled. The current application allows increased surface exposure of the coating liquid to the surface of the bone particle, which in turn allows increased sporadic mineral nucleation on the surface of the bone particle.

In some embodiments, in the coating process, the meshes can have the same size openings. In some embodiments, the meshes can have different size openings from each other and can be used in the coating process. In some embodiments, a mesh can be stacked that does not have bone particles thereon and will allow coating liquid to pass through its openings.

In some embodiments, when different size meshes are used, the different size meshes also allow bone particles of different sizes to be isolated on meshes that have smaller openings than the bone particles. This allows reduction in bone particle wastage as the bone particles can be captured on the mesh. The meshes also allow spacing of the bone particles and reduce the chance of the bone particles hitting each other, which can disrupt the integrity of the coating.

Figure 1A:
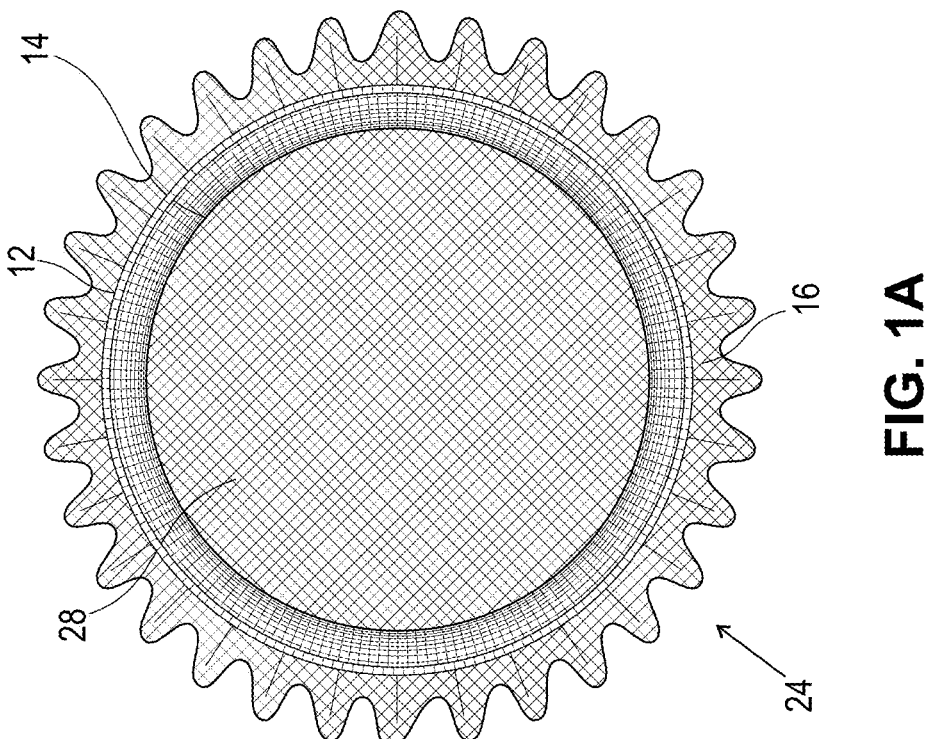
FIG. 1A is a top view of one embodiment of a stackable mesh shown in an unstacked configuration. A single mesh is shown. The mesh comprises openings that allow bone particles to be coated in a single layer. The bone particles are not shown.

FIG. 1A is a top view of one embodiment of a stackable mesh shown in an unstacked configuration 24. The first mesh 10 comprises a first set of openings 28 that allow bone particles to be coated in a single layer. The first mesh comprises a top portion 12, a bottom portion 14, and can optionally have a housing 16. The housing 16 can partially enclose the first mesh as shown and help aid not only in stacking the mesh but also allowing the transfer of the bone particles after they are coated to a drying area (e.g., oven). In some embodiments, the top portion of the first mesh can be configured to have another mesh, usually a mesh with larger openings, stacked above it. The top portion 12 of the mesh also has an area where bone particles and coating liquid can be introduced. In some embodiments, the method uses only one single mesh.

FIG. 1B is a side view of one embodiment of stackable meshes. Here two meshes are shown in a stacked configuration 30. The first mesh 10 (top mesh) has a first set of openings 28 that are larger in size than a second set of openings 29 of the second mesh 18 (lower mesh). The first mesh comprises a top portion 12, a bottom portion 14, and can optionally have a housing 16. The top portion 12 of the mesh also has an area where bone particles and coating liquid can be introduced. Second mesh 18 comprises a second set of openings 29 that is smaller in size than the first set of openings 28 of the first mesh. The second mesh comprises a top portion 20, a bottom portion 26, and can optionally have a second housing 22. The second housing 22 can partially enclose the second mesh as shown and help aid not only in stacking the second mesh but also allowing the transfer of the bone particles after they are coated to a drying area (e.g., oven). In some embodiments, the top portion 20 of the second mesh can have an area where bone particles and coating liquid can be introduced.

It will be understood that, in some embodiments, in the coating process, a mesh can have the same size openings as the mesh stacked above or below it. The same size mesh can be stacked immediately adjacent to a mesh having the same size openings or stacked intermittently among different layers of the meshes having different size openings. For example, a plurality of meshes having the same size openings can be the first mesh and these meshes can be stacked immediately adjacent to each other or distributed above or below meshes having a smaller size opening or a larger size opening to form a pattern. In some embodiments, the stackable meshes comprise a cover mesh 13 having openings 15 to allow coating liquid with or without bone particles therethrough. The cover mesh can be stacked on top of the first mesh or can be stacked on top of all the other meshes in the stack. In some embodiments, the cover mesh can have no bone particles on it, and the cover mesh can be used to ensure that coating liquid flow is the same to meshes stacked below the cover mesh.

In the embodiment shown in FIG. 1B, the first mesh is stacked directly above the second mesh and bone particles of a larger size than the first set of openings of the first mesh stay on it for contact with the coating liquid. Bone particles of smaller size pass through the first mesh and are captured on the second mesh provided the bone particles are a size larger than the second set of openings of the second mesh, where the bone particles will be contacted with the coating liquid that passes through the first set of openings of the first mesh.

It will be understood by those of ordinary skill in the art that meshes can be stacked above or below each other but do not need to directly contact each other. Therefore, the meshes can be spaced a distance between each other that allows optimum flow of coating liquid and particles from one mesh to the other. In the embodiment shown in FIG. 1B, the housing 16 of the first mesh and the second housing 22 of the second mesh allows the optimal distance for flow of bone particles and coating liquid. In some embodiments, the first mesh can be spaced parallel to the second mesh, where they are both fluidly communicating with each other.

Figure 2:
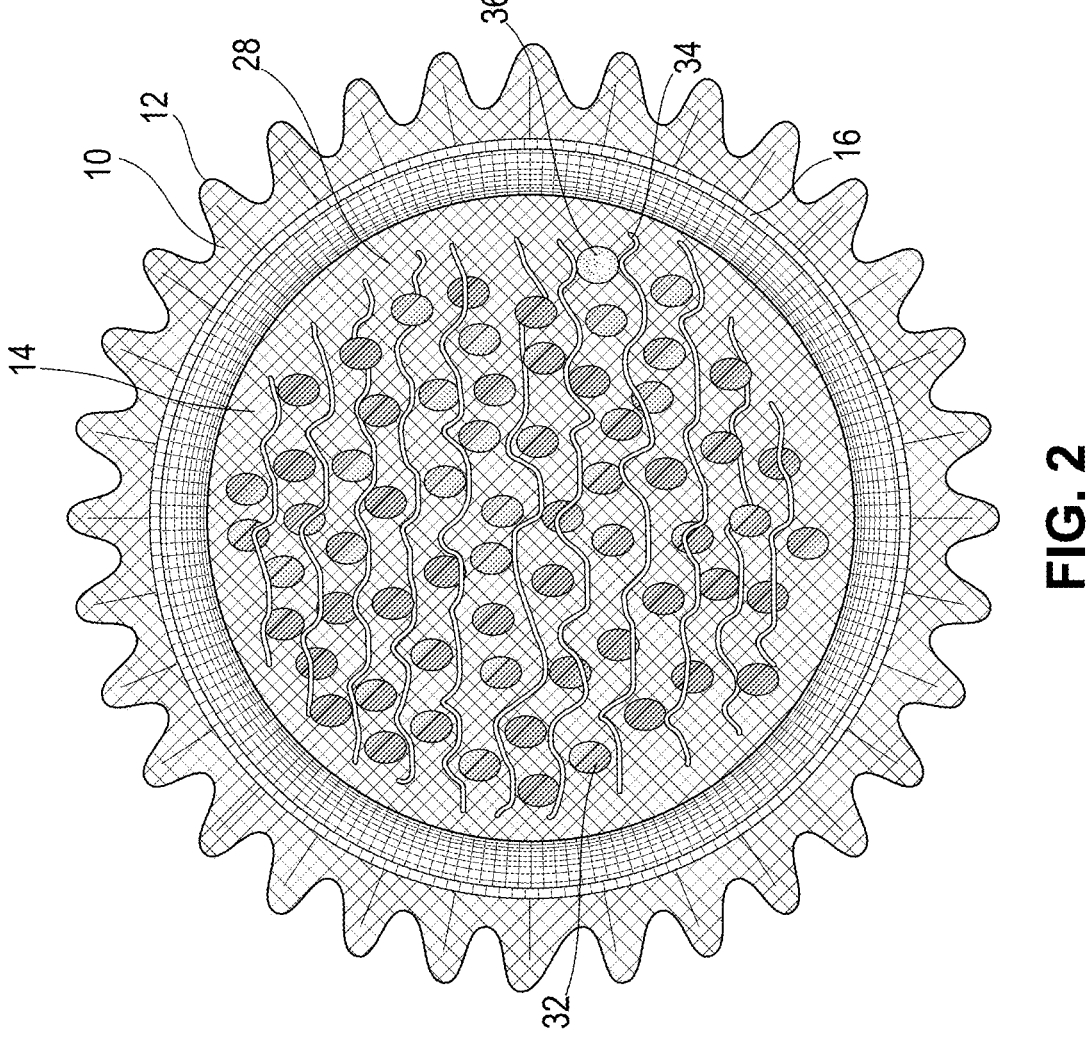
FIG. 2 is a top view of a single stackable mesh loaded with bone particles and having coating liquid contacting the bone particles and causing them to float on the mesh which allows more surface nucleation for the coating of the bone particles. It will be understood that a plurality of meshes (not shown) will be stacked underneath the top mesh shown.

FIG. 2 illustrates a top view of a stackable mesh loaded with bone particles 32 in the process of being coated and having coating liquid 34 contacting the bone particles in the methods and apparatus of the current application. In FIG. 2, the bone particles are disposed on the bottom portion 14 of the first mesh. The bottom portion of the first mesh has a first set of openings 28 that allows smaller bone particles and coating liquid to slowly drain into and be captured by the second mesh (not shown). In this way, the bone particles can have more coated surface by controlled addition of the coating liquid contacting the bone particles causing each individual bone particle to be isolated, submerged, suspended, and/or incubated in the coating liquid in the top portion 12 within the housing 16 of the first mesh 10. It will be understood that a plurality of meshes (not shown) can be stacked below the first mesh, including for example, two, three, four, five, six, seven, eight, nine, ten, eleven, twelve, thirteen, fourteen, fifteen, sixteen, seventeen, eighteen, or more. In some embodiments, the term "above" is referred to a geographical location at a higher level in altitude on a vertical axis. In some embodiments, the term "below" is referred to a geographical location at a lower level in altitude on a vertical axis. Typically, the meshes are stacked on one another substantially parallel to each other.

Shown in FIG. 2, the bone particles are spaced apart on the mesh and the mesh allows less bone particle interaction with each other and maximizes the bone particles surface area with the coating liquid. This allows a uniform incubation and coating of the bone particles to form a coated bone particle 36 on one layer. It will be understood that the bone particles and coating liquid can be added to the mesh in any order. Therefore, the bone particles can be added to the mesh first and then the coating liquid, or the coating liquid can be added to the mesh first and then the bone particles or both the coating liquid and the bone particles can be added to the mesh simultaneously. In some embodiments, the coating liquid and the bone particles can be mixed together and then added to the mesh.

Figure 3A:
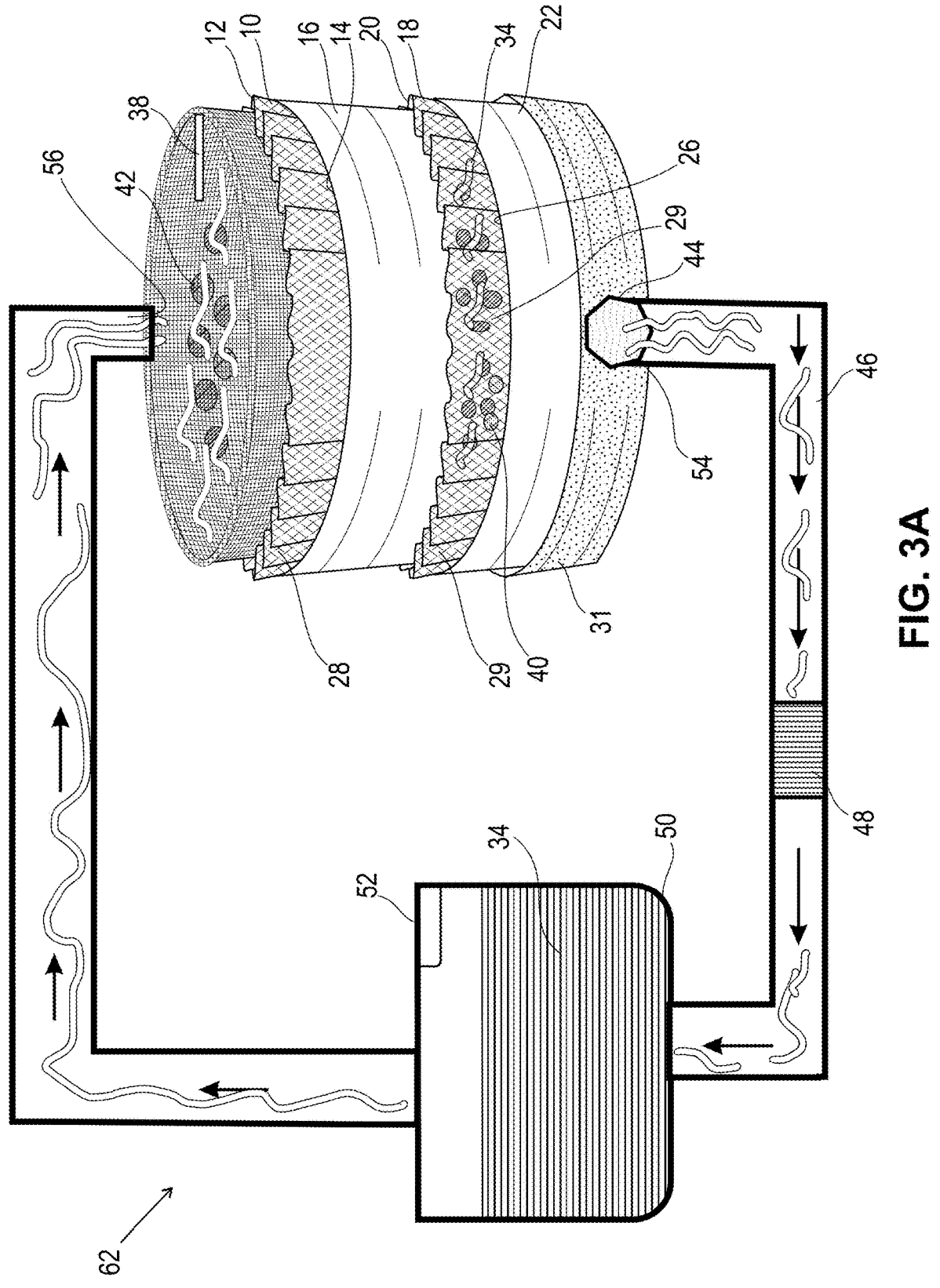
FIG. 3A is a side view of one embodiment of an apparatus of the current application that illustrates the coating of bone particles within a first (top) mesh and second (bottom) mesh shown in a stacked configuration. The apparatus comprises a pump fluidly coupled to a container of coating liquid that directs coating liquid to the first mesh and provides a coating bath to coat larger bone particles in the first mesh and smaller bone particles in the second mesh. Excess coating liquid is recycled or replenished in this embodiment.

Referring to FIG. 3A, an apparatus for coating bone particles is provided using at least two meshes that allow coating of bone particles on each layer of the mesh. The apparatus 62 comprises a plurality of stackable meshes (e.g., a first mesh 10 and a second mesh 18). The first mesh has housing 16 and the second mesh has second housing 22 and the meshes are shown in a stacked configuration. It will be understood by one of ordinary skill in the art that the housing on each mesh is optional.

Bone particles of various sizes are added to the top portion of the first mesh 10. Large bone particles 42 are caught and disposed on the bottom portion 14 of the first mesh. Small bone particles 40 and coating liquid 34 pass through the first set of mesh openings 28 at the bottom portion 14 of the first mesh and flow into the top portion 20 of the second mesh. Small bone particles then are disposed on the bottom portion 26 of the second mesh. The bone particles can have various sizes. The sizes of the large bone particles and the small bone particles are relative to the batch of uncoated bone particles to be used for coating and/or the sizes of the mesh pores. For example, as described in Example 1 below, large bone particles having a size greater than 255 microns will stay in a layer on the first mesh. The first mesh can have a first set of openings less than 255 microns. Bone particles having a size smaller than 255 microns will flow through the first set of openings 28 of the first mesh and flow into the second mesh 18. The smaller bone particles, which have size smaller than 255 microns but larger than 212 microns will stay in layer of the second mesh. Bone particles with sizes smaller than 212 microns and coating liquid will flow through the second set of mesh openings 29 as they are smaller than the second set of mesh openings and flow into the layer of the third mesh (not shown).

In some embodiments, the bone particles with sizes between 212 microns and 160 microns, and all remaining bone particles will be captured and stay on the third mesh in one layer. In some embodiments, the bone particles with sizes between 212 microns and 160 microns will stay on the layer of the third mesh and all the remaining bone particles and coating liquid will pass through the third mesh and flow into a collection container. In some embodiments, whether the remaining bone particles pass through the bottommost layer of the stackable mesh depends on the distribution of bone particles in each layer so maximum spacing between each particle can be achieved to prevent interference of particle interaction during mineralization of the coating liquid on the surface of the bone particles.

In some embodiments, the apparatus further comprises a collection container 31 under or directly below the bottommost mesh (e.g., the second mesh) such that the second set of openings 29 at the bottom of the second mesh allows smaller bone particles and coating liquid to flow through the second set of openings 29 of the second mesh. The collection container 31 can capture excess coating liquid and/or small bone particles, where they can be recirculated back to the meshes.

In some embodiments, the coating liquid can be added to the stackable meshes to fill line 38, which indicates the level of coating liquid that can contact the bone particles so that they can be incubated, submerged, suspended, and/or bathed with coating liquid.

The meshes allow the bone particles to be spread out or distributed loosely away from each other so that each bone particle has a greater surface area exposed to coating liquid.

In the apparatus 62 shown in FIG. 3A, the second housing 22 or the collection container 31 can comprise an outlet 44 that allows drainage of the coating liquid. In the embodiment shown, the outlet 44 is disposed on a sidewall of a housing (e.g., the second housing 22) or a sidewall of the collection container 31. In some embodiments, the outlet comprises a filter (not shown) that prevents the bone particles from flowing out of the stackable meshes.

The apparatus 62 can also comprise a tube 46 fluidly coupled to the outlet 44 at tube inlet 54 that leads to fluid pump 48, which pumps collected coating liquid to tube outlet 56, which delivers the coating liquid back to the stackable meshes. The fluid pump assists in pumping the fluid from the tube inlet through the tube outlet. In this way, collected coating liquid can be recirculated back to the meshes for coating the bone particles.

The apparatus 62 can also comprise a container 50 for storing coating liquid. The container has port 52 that is configured to receive additional coating liquid or replenish coating liquid as illustrated in FIG. 3A.

Figure 3B:
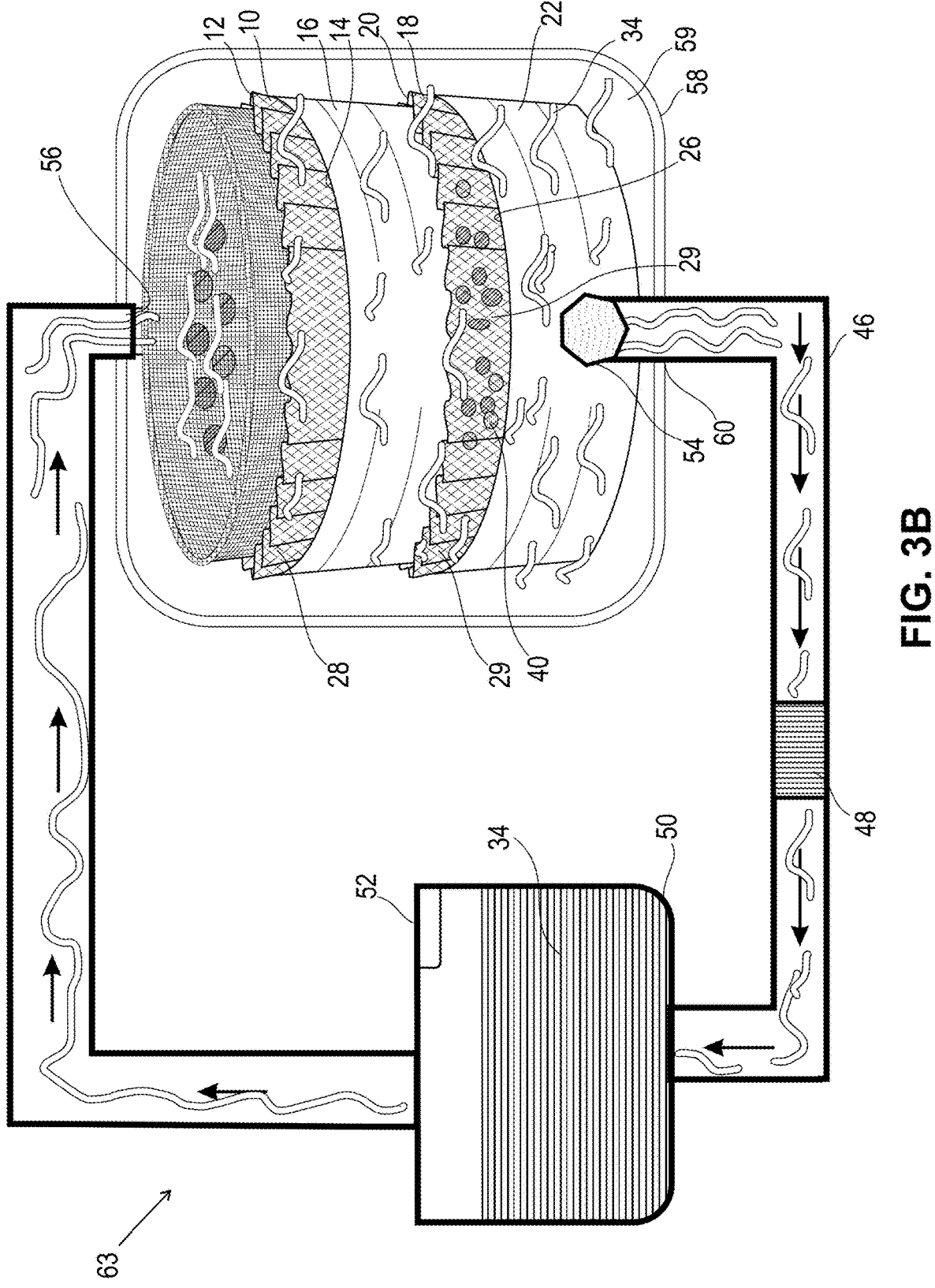
FIG. 3B is a side view of one embodiment of an apparatus of the current application that illustrates the coating of bone particles within a first (top) mesh and second (bottom) mesh shown in a stacked configuration. The apparatus comprises a pump fluidly coupled to a container of coating liquid that directs coating liquid to the first mesh and provides a coating bath to coat larger bone particles in the first mesh and smaller bone particles in the second mesh. In this embodiment, both meshes are submerged in a container. Excess coating liquid is also recycled or replenished in this embodiment.

Referring to FIG. 3B, the second apparatus 63 is similar to the apparatus 62 in FIG. 3A, except in the embodiment of FIG. 3B, a second container 58 is provided. The container is connected to the tube and capable of replenishing additional coating liquid to the stackable meshes. In some embodiments, the apparatus further comprises a second container 58. The second container 58 is configured to hold and partially enclose the stackable meshes. The second container 58 can comprise outlet 60 of the second container. The outlet 60 of the second container can be disposed on a sidewall 59 of the second container. The outlet 60 can be aligned with outlet 44 (not shown) of the second housing 22. This allows the outlet to drain coating liquid to tube 46, which is fluidly coupled to pump 48, which pumps coating liquid out to outlet 56. The apparatus allows coating liquid to be recirculated or replenished. In the embodiment shown in FIG. 3B, the first mesh and the second mesh are immersed in coating liquid in the second container. In some embodiments, the container is configured to enclose at least the first mesh, at least the second mesh, or at least the first and the second mesh.

In some embodiments, the methods and apparatus of the current application can be conducted continuously through continuous pumping and draining of the coating liquid from the second container and/or the bottommost housing of the stackable mesh. In some embodiments, the method can be conducted in a batch process such that coating liquid is all drained before new and/or unused coating liquid is added back into the second container or into the first mesh. In some embodiments, the apparatus can comprise a weight 11 on top and/or above the first mesh to keep the first mesh from overflowing or moving in the second container. The weight can be in various shapes that do not interfere with the additions of the coating liquid and/or bone particles.

After the bone particles are coated, the meshes can be removed and the meshes containing the bone particles can be placed directly into the oven for drying without transferring the coated bone particles from the mesh.

Figure 4:
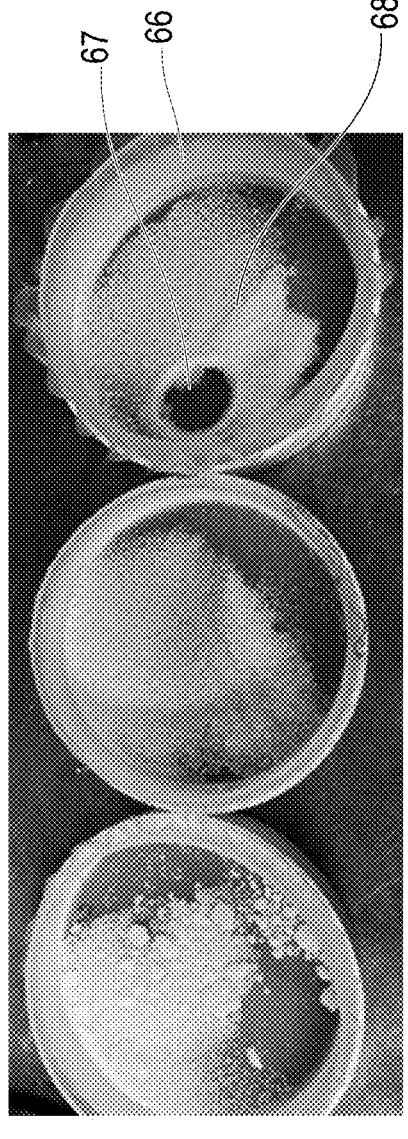
FIG. 4 is a top view of a plurality of stackable meshes separated in an unstacked configuration after the coating process is completed. Each mesh has coated bone particles thereon, and the mesh can oven dried with the coated bone particles on it. These meshes were originally used in the coating process.

FIG. 4 illustrates an embodiment of the stackable meshes in unstacked configuration. The stackable meshes provides the benefit of easy transfer and drying of coated bone particles 68. The coated bone particles maybe dried directly on the mesh that was used to capture and coat the bone particles. The oven dried mesh 66 and an outlet 67 of the housing are shown in FIG. 4. The resulting coated bone particles has a nano-apatite coating on its surface, which increases the surface area of the bone particle as shown in the scanning electron micrograph (SEM) in FIG. 5. In some embodiments, the method comprises drying the coated bone particles remaining on the first mesh, second mesh, third mesh or all of the meshes in an oven.

Bone Particles

Bone particles that can be added to the mesh for coating can include natural bone or synthetic bone in particulate form and can be coated with a polymer (e.g., collagen) before being coated with the liquid coating. Bone particles include natural or synthetic granules, fibers, powder, chips, shards, demineralized bone particles, surface demineralized bone particles, ceramic particles, or a combination thereof. Bone particles, whether natural or synthetic can be in any shape including triangular, oval, oblong, spherical, cube shaped, cylindrical shape, disc shaped, or other shapes having regular, irregular or random geometries.

In some embodiments, the bone particles that can be added to the meshes for coating can be an inorganic material, such as an inorganic ceramic and/or bone substitute material. Exemplary inorganic materials or bone substitute materials include but are not limited to aragonite, dahlite, calcite, brushite, amorphous calcium carbonate, vaterite, weddellite, whewellite, struvite, urate, ferrihydrate, francolite, monohydrocalcite, magnetite, goethite, dentin, calcium carbonate, calcium sulfate, calcium phosphosilicate, sodium phosphate, calcium aluminate, calcium phosphate, hydroxyapatite, alpha-tricalcium phosphate, dicalcium phosphate, β-tricalcium phosphate, tetracalcium phosphate, amorphous calcium phosphate, octacalcium phosphate, BIOGLASS™ fluoroapatite, chlorapatite, magnesium-substituted tricalcium phosphate, carbonate hydroxyapatite, substituted forms of hydroxyapatite (e.g., hydroxyapatite derived from bone may be substituted with other ions such as fluoride, chloride, magnesium sodium, potassium, etc.), or combinations or derivatives thereof.

In some embodiments, the bone particles that can be added to the mesh for coating can comprise mineral particles, which comprise tricalcium phosphate and hydroxyapatite in a ratio of about 80:20 to about 90:10. In some embodiments, the mineral particles can comprise tricalcium phosphate and hydroxyapatite in a ratio of about 70:30 to about 95:5. In some embodiments, the mineral particles can comprise tricalcium phosphate and hydroxyapatite in a ratio of about 85:15.

The bone particles that can be added to the mesh for coating can have a certain size distribution. The most widely used method of describing bone particles size distribution is the D values. The D10, D50 and D90 values are commonly used to represent the midpoint and range of the bone particle sizes of a given sample. In particular, the bone particles size distribution D50 is also known as the median length or diameter or the medium value of the bone particles size distribution; it is the value of the bone particle diameter at 50% in the cumulative distribution, D10 is the size of the bone particle sample below which 10% of the sample lies and D90 is the size of the bone particle sample below which 90% of the sample lies. In some embodiments, the D50 value of the bone particles ranges from 50 to 250 microns.

In some embodiments, the bone particles that can be added to the mesh for coating can have a D10, D50, or D90 size of 250 microns or less. In some embodiments, the bone particles have a particle size of 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132, 134, 136, 138, 140, 142, 144, 146, 148, 150, 152, 154, 156, 158, 160, 162, 164, 166, 168, 170, 172, 174, 176, 178, 180, 182, 184, 186, 188, 190, 192, 194, 196, 198, 200, 202, 204, 206, 208, 210, 212, 214, 216, 218, 220, 222, 224, 226, 228, 230, 232, 234, 236, 238, 240, 242, 244, 246, 248 and/or 250 microns.

In one particular embodiment, suitable bone particles that can be added to the mesh and coated with the coating liquid include MasterGraft® granules and MasterGraft® mini granules made by Medtronic Sofamor Danek, Inc., Memphis, Tenn., which are biphasic, resorbable, ceramic granules comprising about 15% hydroxyapatite (HA) and about 85% beta-tricalcium phosphate (β-TCP). The granules have a natural, interconnected, porous structure which mimics that natural structure of bone and allows for rapid, homogenous bone ingrowth throughout each granule. Each granule is about 80% porous with an average pore size of about 500 microns and about 125 microns interconnected diameter. MasterGraft® granules have an average diameter of about 1.6 mm to about 3.2 mm. In some embodiments, the granules can have an average diameter of about 0.1 mm to about 0.8 mm. MasterGraft® mini granules have an average diameter of about 0.5 mm to about 1.6 mm. Through a highly porous granular structure and the 15% HA/85% β-TCP chemical composition, MasterGraft® granules and MasterGraft® mini granules facilitate rapid, homogenous osseointegration, which supports the bone healing process by acting as a scaffold over which bone can grow. The porosity of the material provides an excellent basis for vascularization and penetration of associated cells, which support integration of the substitute materials required for healing while preserving the bony architecture and attached gingiva.

Figure 6:
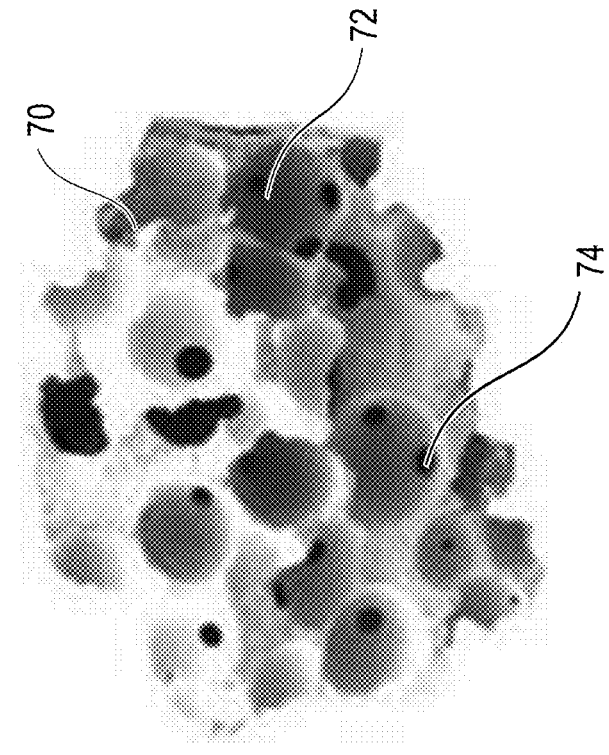
FIG. 6 is a photo of a bone particle, for example, a micron-sized Mastergraft® granule (left) before being coated and an enhanced photo (25× magnification) of that granule showing macro-pores and micro-pores (right).
Figure 6:
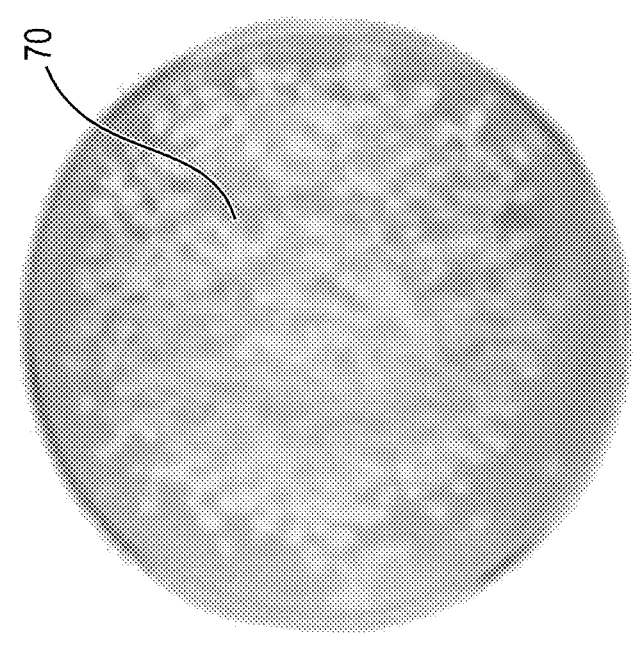

FIG. 6 is a photo of a micron-sized Mastergraft® granule 70 (left) before being coated and an enhanced photo (25× magnification) of that granule showing macro-pores 72 and micro-pores 74 (right).

In some embodiments, the bone particles to be coated or the coated bone particles can have macropores having a diameter in a range from about 10, 20, 30, 40, 50, 60, 70, 80, 90, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795 to about 800 μm. In some embodiments, the diameter of each of the micropores can be from about 0.01, 0.02, 0.03, 0.04, 0.05, 0.06, 0.07, 0.08, 0.09, 0.1, 0.2, 0.3, 0.4, 0.6, 0.7, 0.8, 0.9, 1, 2, 3, 4, 5, 6, 7, 8, 9 to about 10 microns.

In some embodiments, the bone particles to be coated or the coated bone particles can have a percent microporosity from about 10 to about 100% or from about 10, 20, 30, 40, 50, 60, 70, 80, 90 to about 100%. In some embodiments, micropores can have a diameter in a range from about 50 μm to about 800 μm. In some embodiments, micropores have a diameter in range from about 10, 20, 30, 40, 50, 60, 70, 80, 90, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795 to about 800 μm.

In some embodiments, the bone particles to be coated can comprise a ceramic material in an amount from about 50 to about 98 wt. % and also a polymer in an amount from about 2 to about wt. % based on a total weight of each of the bone particles as more particularly described in U.S. application Ser. No. 17/018,708 filed Sep. 11, 2020 and assigned to Warsaw Orthopedic, Inc., and published as US20210069382, which is incorporated herein by reference in its entirety. The plurality of bone particles can each include from about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97 to about 98 wt. % ceramic material and from about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 to about 50 wt. % polymer based on the total weight of each of the bone particles. The ceramic material can comprise synthetic ceramic or ceramics including hydroxyapatite and beta-tricalcium phosphate. The ceramic material can be in a powder form. The ceramic material can comprise a calcium to phosphate ratio of between 1.0 to about 2.0. In some embodiments, the calcium to phosphate ratio is between 1.0, 1.1, 1.2, 1.3, 1.4, 1.5, 1.6, 1.7, 1.8, 1.9 to about 2.0.

The ceramic material of the bone particles can be a biphasic calcium phosphate comprising hydroxyapatite in an amount of about 8 to about 22 wt. % and beta-tricalcium phosphate in an amount of about 78 to about 92 wt. %. In some embodiments, the hydroxyapatite is in an amount of about 8, 9, 10, 11, 12, 13, 14, 15, 16, 17, 18, 19, 20, 21 to about 22 wt. % and the beta-tricalcium phosphate in an amount of about 78, 79, 80, 81, 82, 83, 84, 85, 86, 87, 88, 89, 90, 91 to about 92 wt. %.

The porous ceramic particles can comprise hydroxyapatite and beta-tricalcium phosphate. The hydroxyapatite can be in an amount of about 8 to about 22 wt. % based on a total weight of a ceramic granule. The hydroxyapatite can be in a range from about 8, 9, 10, 11, 12, 13, 14, 15, 16, 17, 18, 19, 20, 21 to about 22 wt. %. In some embodiments, the hydroxyapatite can be in a range from about 1 to about 99 wt. %, such as from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 to about 99 wt. %.

The beta-tricalcium phosphate can be in an amount of about 78 to about 92 wt. % based on a total weight of a ceramic granule. The beta-tricalcium phosphate can be in an amount from about 78, 79, 80, 81, 82, 83, 84, 85, 86, 87, 88, 89, 90, 91 to about 92 wt. %. In some embodiments, the beta-tricalcium phosphate can be in a range from about 1 to about 99 wt. %, such as from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 to about 99 wt. %.

The porous ceramic particles can have a calcium to phosphate ratio of between 1.0 to about 2.0. In some embodiments, the calcium to phosphate ratio is between 1.0, 1.1, 1.2, 1.3, 1.4, 1.5, 1.6, 1.7, 1.8, 1.9 to about 2.0.

In some embodiments, the ceramic particles coated with a coating liquid, such as for example, a mineral coating can be embedded in a porous carrier matrix such as cross-linked or non-crosslinked collagen, carboxymethyl cellulose or alginate that can also include identification or surface markers that distinguish them from uncoated ceramic particles.

The polymer component of each of the plurality of bone particles can be porcine or bovine collagen, bovine type I collagen, tendon or dermis derived collagen, or a combination thereof.

Each of the plurality of bone particles to be coated with a coating liquid or that have been coated with a coating liquid can have an average diameter from about 0.1 mm to about 10 mm. For example, each of the bone particles can have an average diameter from about 0.05, 0.1, 0.2, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9 to about 10 mm. In some embodiments, the bone particles can have a granule size from about 0.09 mm to about 0.8 mm.

Each of the bone particles to be coated with a coating liquid or that have been coated with a coating liquid can have an average height and/or length from about 0.05, 0.01 mm to about 10 mm or from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9 to about 10 mm.

The ceramic material provided in each of the bone particles to be coated with a coating liquid or that have been coated with a coating liquid can be in the form of porous ceramic granules. Exemplary porous ceramic granules suitable for use with the current application include the granules described in U.S. application Ser. No. 16/523,259, filed on Jul. 26, 2019 and assigned to Warsaw Orthopedic, Inc., which is published as US20210023258A1 and is incorporated herein by reference in its entirety. The porous ceramic granules to be coated with a coating liquid or that have been coated with a coating liquid can have an average diameter from about 50 μm to 1.6 mm. In some embodiments, the average diameter of the granules may be from about 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795, 800, 850, 900, 950, 1000, 1100, 1150, 1200, 1250, 1300, 1350, 1400, 1450, 1500, 1550 to about 1600 μm.

Each of the porous ceramic granules to be coated with a coating liquid or that have been coated with a coating liquid can have a Brunauer-Emmett-Teller (BET) surface area from about 0.2 to about 10 m$^2$/g. The BET surface area can be from about 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to about 100 $m^2/g$. The increase in surface area further facilitates new bone growth by allowing the granules to dissolve and release calcium faster than ordinary granules would.

Each of the porous ceramic granules to be coated with a coating liquid or that have been coated with a coating liquid can have a microporosity, and the diameter of the micropores is from about 0.01 to about 10 microns. In some embodiments, the diameter of each of the micropores can be from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9 to about 10 microns. In some embodiments, the median pore diameter can be about 125 μm and the average pore diameter can be 78 μm.

The plurality of bone particles to be coated with a coating liquid or that have been coated with a coating liquid can be made into a variety of shapes after lyophilization or using cryogel applications. The shapes can be cut from a textured or flat shaped sheet of bone particles comprising the ceramic material and polymer or can be prepared as individual bone particle created in molds.

The bone particle to be coated with a coating liquid or that have been coated with a coating liquid are porous, but in some embodiments, the bone particles are highly porous. For example, porous bone particles can have a porosity from about 10 to about 80% or from about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 to about 80%. Highly porous bone particle can have a porosity from about 81 to about 99% or from about 81, 82, 83, 84, 85, 86, 87, 88, 89, 90, 91, 92, 93, 94, 95, 96, 97, 98 to about 99%.

In some embodiments, additional or alternative materials may be added to the bone particles after they are coated with the coating liquid such as one or more of poly (alpha-hydroxy acids), polyglycolide (PG), polyethylene glycol (PEG) conjugates of poly (alpha-hydroxy acids), poly-orthoesters (POE), polyaspirins, collagen, polyphosphagenes, gelatin, hydrolyzed gelatin, fractions of hydrolyzed gelatin, elastin, starch, pre-gelatinized starch, hyaluronic acid, chitosan, alginate, albumin, fibrin, vitamin E analogs, such as alpha tocopheryl acetate, d-alpha tocopheryl succinate, D,L-lactide, or L-lactide, caprolactone, dextrans, vinylpyrrolidone, polyvinyl alcohol (PVA), PVA-g-PLGA, PEGT-PBT copolymer (polyactive), methacrylates, PEO-PPO-PAA copolymers, PLGA-PEO-PLGA, PEG-PLG, PLA-PLGA, poloxamer 407, PEG-PLGA-PEG tri-block copolymers, POE, SAIB (sucrose acetate isobutyrate), polydioxanone, methylmethacrylate (MMA), MMA and N-vinylpyyrolidone, polyamide, oxycellulose, copolymer of glycolic acid and trimethylene carbonate, polyesteramides, polyether ether ketone, polymethylmethacrylate, silicone, hyaluronic acid, or combinations thereof.

In some embodiments, the bone particles after coating with a coating liquid can comprise at least one biodegradable polymer comprising one or more of collagen, poly (lactide-co-glycolide) (PLGA), polylactide (PLA), polyglycolide (PGA), D-lactide, D,L-lactide, L-lactide, D,L-lactide-co-ε-caprolactone, L-lactide-co-ε-caprolactone, D,L-lactide-co-glycolide-co-ε-caprolactone, poly(D,L-lactide-co-caprolactone), poly(L-lactide-co-caprolactone), poly(D- lactide-co-caprolactone), poly(D,L-lactide), poly(D-lactide), poly(L-lactide), poly(esteramide), carboxymethylcellulose (CMC), alkylene oxide copolymer (AOC) or a combination thereof.

The collagen added to the coated bone particles can be from skin, tendon, fascia, ligament, trachea, or organ collagen. In certain embodiments, the collagen is human collagen or another mammalian collagen (e.g., porcine, bovine, or ovine). The collagen can be sourced from any animal.

Generally, there are about twenty-eight distinct collagen types that have been identified in vertebrates, including bovine, ovine, porcine, chicken, marine, and human sources. The collagen types are numbered by Roman numerals, and the chains found in each collagen type are identified by Arabic numerals. Detailed descriptions of structure and biological functions of the various types of naturally occurring collagens are generally available in the art.

The collagen may have the same composition as in naturally occurring sources. Examples of sources of collagens include human or non-human (bovine, ovine, and/or porcine), as well as recombinant collagen or combinations thereof. Examples of suitable collagen include, but are not limited to, human collagen type I, human collagen type II, human collagen type III, human collagen type IV, human collagen type V, human collagen type VI, human collagen type VII, human collagen type VIII, human collagen type IX, human collagen type X, human collagen type XI, human collagen type XII, human collagen type XIII, human collagen type XIV, human collagen type XV, human collagen type XVI, human collagen type XVII, human collagen type XVIII, human collagen type XIX, human collagen type XXI, human collagen type XXII, human collagen type XXIII, human collagen type XXIV, human collagen type XXV, human collagen type XXVI, human collagen type XXVII, and human collagen type XXVIII, or combinations thereof. Collagen may further or alternatively comprise hetero- and homo-trimers of any of the above-recited collagen types. In some embodiments, the collagen comprises hetero- or homo-trimers of human collagen type I, human collagen type II, human collagen type III, or combinations thereof. In some embodiments, the collagen is type I or substantially all is collagen type I, e.g., at least 60%, at least 65%, at least 70%, at least 75%, at least 80%, at least 85%, at least 90%, or at least 95%.

Coating Liquid

The coating liquid that is coated on the bone particle imparts increased surface area to that bone particle. In some embodiments, the increased surface area increases the hydrophilic properties of the coated bone particles and makes the bone implant formed from those coated bone particles more hydrophilic and more osteoinductive and osteoconductive allowing the implant to better integrate with the bone defect.

The coating liquid is flowable and can contact the bone particles in a controlled manner by incubating, submerging, suspending and/or bathing the coating liquid in those bone particles. The coating liquid can comprise a mineral component, a polymer component, an organic component a solvent, a buffer, or a combination thereof.

In some embodiments, the coating liquid comprises a calcium-containing mineral, the calcium-containing mineral is at least one of apatite, hydroxyapatite (HAP), α-tricalcium phosphate, β-tricalcium phosphate, amorphous calcium phosphate, dicalcium phosphate, octacalcium phosphate, calcium carbonate, a carbonated-substituted calcium-deficient hydroxyapatite, anorganic bone or combinations thereof. Anorganic bone refers to bone mineral only, with the organic constituents removed.

The calcium-containing mineral can comprise a plurality of layers, e.g., separate layers having distinct dissolution profiles. Under physiological conditions, solubility of calcium phosphate species can adhere to the following solubility trend: amorphous calcium phosphate>dicalcium phosphate>octacalcium phosphate>β-TCP>HAP. A dicalcium phosphate mineral can have a dissolution rate that is more than fifty times higher than that of HAP. Therefore, creation of a matrix with distinct calcium phosphate coatings allows for a broad range of dissolution patterns.

The mineral coating can impart to the bone particle spherical clusters with a plate-like structure or a plate-like structure and a carbonate-substituted, calcium-deficient hydroxyapatite phase structure. As another example, the coating can be an osteoconductive mineral coating and allows osteoclasts and osteoblasts to remodel bone.

The mineral coating useful for coating the bone particles can include at least about 1% or at least about 100% porosity including all discrete values included in this range. The mineral coating can also include a pore diameter from about 1 nm to about 3500 nm including all discrete values included in this range. The mineral coating useful in this application can include a ratio of at least about 0.1 Ca/P to about 10 Ca/P including the discrete values included in this range.

As another example, the mineral coating can include an apatite or an amorphous apatite. Apatite can include calcium phosphate, calcium carbonate, calcium fluoride, calcium hydroxide, calcium citrate or a combination thereof.

As another example, a mineral coating can comprise a plurality of discrete mineral islands on the bone particles, or the mineral coating can be formed on the entire surface of the bone particles. As another example, the mineral coating can comprise a substantially homogeneous mineral coating. In other embodiments, the mineral coatings can be a calcium-deficient carbonate-containing hydroxyapatite.

As another example, the mineral coating can include hydroxyapatite. Calcium-deficient (non-stochiometric) hydroxyapatite, $Ca_{10-x}(PO_4)_{6-x}(HPO_4)_x(OH)_{2-x}$ (where x is between 0 and 1) has a Ca/P ratio between 1.67 and 1.5. The Ca/P ratio is often used in the discussion of calcium phosphate phases. Stoichiometric apatite $Ca_{10}(PO_4)_6(OH)_2$ has a Ca/P ratio of 10:6 normally expressed as 1.67. The non-stoichiometric phases have the hydroxyapatite structure with cation vacancies $(Ca^{2+})$ and anion $(OH^-)$ vacancies. Hydroxyapatite can be predominantly crystalline, but, in some cases, may be present in amorphous forms. The mineral coatings useful in this application can include from at least about 1% to at least about 100% hydroxyapatite, including the discrete values included in this range.

It is known that the hydroxyapatite within the bones of living organisms are very thin plate-like carbonate structures which have an average of 50 nm length, 2-3 nm thickness and a width of 25 nm (see, for example, Heliyon, Volume 6, Issue 4, 2020, Article e03655). In some embodiments, the surface coating on the bone particles is designed to have these characteristics.

In some embodiments, the mineral coating can include octacalcium phosphate. Octacalcium phosphate has a chemical formula of $Ca_8H_2(PO_4)_6 \cdot 5H_2O$ or can also be written as $Ca_4HO_{12}P_3$. Octacalcium phosphate has been shown to be a precursor to hydroxyapatite. Hydrolysis of octacalcium phosphate can create hydroxyapatite. Octacalcium phosphate can be predominantly crystalline, but, in some cases, may be present in amorphous forms. The mineral coating, in some embodiments, can include at least about 1% to at least about 100% octacalcium phosphate including the discrete values included in this range.

In some embodiments, before coating bone particles, the bone particles are first cleaned in a caustic bath, rinsed, and then contacted (e.g., incubated, submerged, suspended and/or bathed) with the coating liquid, which can comprise a modified simulated bodily fluid (mSBF).

Ways to make mSBF coating liquid useful for the current application is described in U.S. application Ser. No. 15/060, 547 filed Mar. 3, 2016, which is assigned to Warsaw Orthopedic, Inc. and published as US20160271296A1, and is described in U.S. application Ser. No. 13/879,178 filed Sep. 25, 2009, which is assigned to Warsaw Orthopedic, Inc., and published as US20140161886A1. These entire disclosures are incorporated herein by reference in their entireties and describe how to make a mineral coating having a plate-like nanostructure on a substrate. These patent applications also describe the formation of a plate-like nanostructure comprising nanoparticles having a size range from about 100 to about 500 nanometers.

In some embodiments, the plate-like nanostructure on the coated bone particle comprises nanoparticles having a size range from about 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 230, 240, 250, 260, 270, 280, 290, 300, 310, 320, 330, 340, 350, 360, 370, 380, 390, 400, 410, 420, 430, 440, 450, 460, 470, 480, 490, to about 500 nanometers. In some embodiments, the plate-like nanostructure on the coated bone particle comprises nanoparticles having a size range from about 5 to about 500 nanometer. In some embodiments, the plate-like nanostructure on the coated bone particle comprises nanoparticles having a size range from about 50 to about 200 nanometer. In some embodiments, the plate-like nanostructure on the coated bone particle comprises nanoparticles having a size range from about 100 to about 200 nanometer. The mSBF provides a calcium and phosphate-rich environment to facilitate crystallization.

In one embodiment, the bone particles comprise Master-Graft® granules made by Medtronic Sofamor Danek, Inc., Memphis, Tenn., which are biphasic, resorbable, ceramic granules comprising about 15% hydroxyapatite (HA) and about 85% beta-tricalcium phosphate (β-TCP). The granules have a natural, interconnected, porous structure which mimics that natural structure of bone and allows for rapid, homogenous bone ingrowth throughout each granule. Each granule is about 80% porous with an average pore size of about 500 microns and about 125 microns interconnected diameter.

To coat MasterGraft® granules, they are suspended in the coating liquid, which can be a mSBF. A recirculating bath is used to maintain physiologic temperature as well as ensure that a controlled rate of interaction between mSBF and the granules occurs throughout the coating process. The stackable meshes allow for an increased density of material within the container while maintaining mSBF flow around the granules. The mSBF can be refreshed every day for example three days, and then rinsed with water and dried. In some embodiments, mSBF is refreshed frequently from about every 1 hour to every 12 hours. In some embodiments, mSBF is refreshed from about every 1, 2, 3, 4, 5, 6, 7, 8, 9, 10, 11, 12, 13, 14, 15, 16, 17, 18, 19, 20, 21, 22, 23 to about 24 hours. In some embodiments, mSBF is refreshed every 2 hours.

Once coating is complete, the meshes allow transfer of the coated granules directly to an oven for drying. As a result, the individual granules are prevented from interacting with each other and disrupting the growth of the nano-apatite plates that are coated on the surface of the granules. The coating on the surface of the bone particles can be a nano sized coating having a nano-coating thickness and/or nano-coating structure.

In some embodiments, the nano-coating thickness ranges from about 1 nm to about 1000 nm. In some embodiments, the thickness ranges from about 50 to about 200 nm. In some embodiments, the thickness ranges from about 40, 45, 50, 55, 60, 65, 70, 75, 80, 85, 90, 95, 100, 105, 110, 115, 120, 125, 130, 135, 140 145, 150, 155, 160,165, 170, 175, 180, 185, 190, 195, 200, 205, 210, 215, to about 220 nm.

In some embodiments, the liquid coating can be a mineral coating (e.g., mSBF) that also contains a polymer and a solvent. The polymer can be acrylic resin, alginate, capro-lactone, collagen, chitosan, hyaluronic acid, hydrogel, hydroxybutyric acid, polyanhydride, polycaprolactone (PCL), poly(dimethylglycolic acid), polydioxanone (PDO), polyester, polyethylene, poly(ethylene glycol), poly(gly-colide) (PGA), poly(glycolic acid), polyhydroxobutyrate, poly(2-hydroxyethyl-methacrylate), poly-lactide-co-gly-colide (PLCG), poly(D,L-lactide-co-glycolide) (PLG), poly (lactide-co-glycolic acid) (PLGA), polylactide (PLA), poly-lactic acid (PLLA), poly-lactide-co-glycolide (PLCG), poly (methylethylglycolic acid), polymethylmethacrylate, polyphosphazenes, polyphosphoesters, polypropylene, poly (propylene fumarate), polyurethane (PU), or silicone rubber, or combinations or copolymers thereof. In some embodi-ments, the polymer in the mineral coating includes a ratio of about 1:1 of two polymers or a polymer and co-polymer thereof. In some embodiments, the polymer in the mineral coating has a grain size of about 10 μm to about 500 μm or an average grain size of about 10 μm to about 500 μm.

In some embodiments, a solvent can be used in the mineral coating. A suitable solvent that can be used in the mineral coating, includes, but is not limited to acetic acid, alcohol, aliphatic ether, aniline, chloroform, chlorinated hydrocarbon, aromatic hydrocarbon, aqueous alkali, aque-ous solution of cupriethylenediamine, benzene, biphenyl, chlorinated aliphatic hydrocarbon, chlorinated hydrocarbon, chloroform, chlorophenol, chlorobenzene, cyclohexanone, chlorinated hydrocarbon, chloroauric acid, DCM, dimethyl-formamide (DMF), DMSO, dichlorobiphenyl, dioxane, dilute aqueous sodium hydroxide, 1,2-dichlorobenzene, dichloromethane, DCM, ethanol, ethyl acetate, ethylene carbonate, esters, formic acid, glycols, halogenated hydro-carbons, HFIP, higher aliphatic ester, higher aliphatic ketone, halogenated hydrocarbon, higher aliphatic ester, higher aliphatic ketone, ketone, higher ketone, hydrocarbon, isopropylamine, methyl ethyl ketone, morpholine, methyl-ene chloride, methanol, methyl ethyl ketone, m-Cresol, NMP, phenol, phenylenediamine, sulfuric acid, tetramethy-lurea, toluene, trifluoroacetic acid, THD, tetramethylurea, tetrahydrofuran (THF), trifluoroacetic acid, trichloroethanol, toluene, trichloroethane, trichloroacetaldehyde hydrate, per-fluorokerosene, pyridine, phenyl ether, piperazine, pyridine, water, or xylene, or combinations thereof.

In some embodiments, the solvent is selected from 2 or more of the following solvents: chloroform, acetic acid, formic acid, or a combination of formic acid and acetic acid. In some embodiments, the ratio of the two solvents is 4:1, 3:1, 2:1, or 1:1.

In some embodiments, the percent weight of polymer to volume of solvent is about 1% w/v to about 10% w/v; or about 1% w/v, about 2% w/v, about 3% w/v, about 4% w/v, about 5% w/v, about 6% w/v, about 7% w/v, about 8% w/v, about 9% w/v, or about 10% w/v.

In some embodiments, the coating liquid comprises a calcium-containing mineral and further includes NaCl, KCl, $MgCl_2$, $MgSO_4$, $NaHCO_3$, $CaCl_2$, $KH_2PO_4$, or a combina-tion thereof to form the modified simulated body fluid.

In some embodiments, the coating liquid comprises a calcium-containing mineral and further comprises: (i) NaCl has a concentration of about 100 mM to about 200 mM; (ii) KCl has a concentration of about 1 mM to about 8 mM; (iii) $MgCl_2$ has a concentration of about 0.2 mM to about 5 mM; (iv) $MgSO_4$ has a concentration of about 0.2 mM to about 5 mM; (v) $NaHCO_3$ has a concentration of about 1 mM to about 100 mM; (vi) $CaCl_2$ has a concentration of about 2 mM to about 20 mM; and (vii) $KH_2PO_4$ has a concentration of about 0.5 mM to about 10 mM. In some embodiments of the method, (i) NaCl has a concentration of about 141 mM; (ii) KCl has a concentration of about 4.0 mM; (iii) $MgCl_2$ has a concentration of about 1.0 mM; (iv) $MgSO_4$ has a concentration of about 0.5 mM; (v) $NaHCO_3$ has a concen-tration of about 4.2 mM; (vi) $CaCl_2$ has a concentration of about 5 mM; and (vii) $KH_2PO_4$ has a concentration of about 2.0 mM to form the mSBF.

In some embodiments, the simulated body fluid includes a buffer comprising DPBS, Tris, Tris-HCl, Tris-buffered saline, PBS, or a combination thereof. The buffer can be at a concentration of about 3 mM to about 40 mM.

In some embodiments, the mineral coating includes (i) about 9% to about 100% hydroxyapatite; (ii) about 90% to about 100% hydroxyapatite; or (iii) about 97% hydroxyapa-tite. In some embodiments, the mineral coating includes (i) about 0% to about 30% octacalcium phosphate; (ii) about 0% to about 3% octacalcium phosphate; or (iii) about 3% octacalcium phosphate. In some embodiments, the mineral coating includes a porosity of (i) between about 2% and about 100%; or (ii) between about 20% and about 28%. In some, the mineral coating includes (i) a pore diameter of between about 1 nm and about 3500 nm pore; or (ii) between about 100 nm and about 350 nm pore diameter.

In some embodiments, the bone particles to be coated include a pore diameter (i) between about 200 μm and about 525 (ii) between about 25 μm to about 65 μm; or (iii) more than about 50 μm. In some embodiments, the bone particle includes a macrochannel length of more than about 100 In some embodiments, the mineral coating includes (i) about 0.1 to about 18 Ca/P, or (ii) about 1.1 to about 1.76 Ca/P (calcium to phosphate ratio). In some embodiments, the mineral coating includes (i) about 1.67 to about 1.76 Ca/P, (ii) about 1.1 to about 1.3 Ca/P, or (iii) about 1.37 to about 1.61 Ca/P.

In some embodiments, the mineral coating liquid includes a crystallinity of (i) about 9% to about 100%; (ii) about 90% to about 100%; or (iii) about 96.5%.

The bone particles can be coated with a mineral coating liquid by incubating the bone particles with the mineral coating liquid. For example, in some embodiments, the mineral coating liquid, described herein, can be made by incubating the bone particles in modified simulated body fluid (mSBF) for four days or more at a pH of about 6.8 to about 7.4 and at a temperature of about 37° C. The mSBF can be refreshed daily. In general, an increase in pH can favor hydroxyapatite growth, while a decrease in pH can favor octacalcium phosphate mineral growth.

In other embodiments, conditions favorable for hydroxy-apatite formation can include a pH between about 5.0 and about 8.0 and a calcium concentration multiplied by a phosphate concentration between about $10^{-5}$ and about $10^{-8}$ M. Conditions favorable for octacalcium phosphate formation include a pH between about 6.0 and about 8.0 and a calcium concentration multiplied by a phosphate concentration between about $10^{-5}$ and about $10^{-7.5}$ M. Furthermore, conditions favorable for dicalcium phosphate dehydrate formation can include a pH between about 6.0 and about 8.0 and a calcium concentration multiplied by a phosphate concentration between about $10^{-4}$ and about $10^{-6}$ M.

In yet other embodiments, the pH of mSBF can be varied between about 5.0 and about 6.0 to promote hydroxyapatite formation. Similarly, the pH of mSBF can be varied between about 6.0 and about 6.5 to promote octacalcium phosphate and hydroxyapatite formation. Likewise, the pH of mSBF can be varied between about 6.5 and about 8.0 to promote dicalcium phosphate, octacalcium phosphate, and hydroxyapatite formation.

In some embodiments, the period of time sufficient to form coated bone particle is about 1 day to about 4 days. In some embodiments, incubating the coating liquid with the bone particles to form nanostructurally coated bone particles can be done for a period of time for at least about 1 day; at least about 2 days; at least about 3 days; or at least about 4 days; or at least about 5 days; or at least about 6 days; or at least about 7 days.

In some embodiments, the coating liquid (e.g., mSBF) that is contacting the bone particles, is maintained, replaced, replenished, removed, or has components added to it including for example, polymer, solvent, buffer, or a combination thereof. In some embodiments, maintaining the concentration of modified simulated bodily fluid includes replacing, replenishing, removing, or adding to modified simulated body fluid at least one of NaCl, KCl, $MgCl_2$, $MgSO_4$, $NaHCO_3$, $CaCl_2$, or $KH_2PO_4$, or a combination thereof. This can be done using the apparatus of FIG. 3A or FIG. 3B.

In some embodiments, the coated bone particles are dried under conditions sufficient to form a continuous coating, which include heating the coated bone particles to about 50° C. to about 200° C., sufficient to soften, melt, or cure the coating on the bone particles.

In some embodiments, the method further includes heating the coated bone particles for about 1 hour to about 6 hours, sufficient to soften, melt, or cure the coating on the bone particles.

In many embodiments, the mineral coating covering the plurality of bone particles comprises a plate-like nanostructure comprising nanoparticles having a size range from about 100 to about 200 nanometers. In some embodiments, the size range of the nanoparticles can be form about 10 to about 100 nanometers.

The coated bone particle shapes and sizes create a high level of surface area, which increases uniform hydration when fluid is administered to the bone particles. For example, due to the high level of surface area, fluid will rapidly move into the bone particles through wicking. The bone particle shapes can include cylinders, cubes, rods, or tubes (e.g., solid or hollow tubes); a half hemispherical hollow tube; a rectangle or rectangles; a disc or discs; electro-spun fibers or a combination thereof. The coated bone particles can also be lyophilized.

Figure 7:
FIG. 7 is an SEM comparing bone particles (e.g., granules) in their uncoated form (left) and nano-apatite bone particles (e.g., granules) in their coated form (right).
Figure 7:
Figure 7:
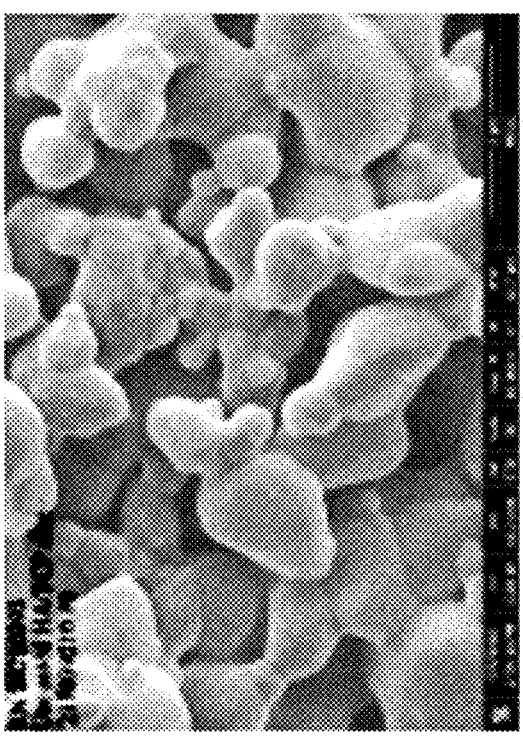

In one embodiment, after the coating process was performed on MasterGraft® granules, scanning electron microscope images in FIG. 7 demonstrated that the plate-like nanotopography of the coating is undamaged on those coated granules. The coated granules were compared to uncoated MasterGraft® granules at a scale bar of 3 μm, also shown in FIG. 7. It was evident that the bone particles coated with a nano-apatite surface coating had an improved surface area of from about 5.31 to about 8.83 $m^2/g$, which represents about an 1106% increase to about an 1840% increase in surface area (an average of 1300%) as exemplified in FIG. 8B as compared to conventional coating processes exemplified in FIG. 8A. The incubation time of the coating process in accordance with the present application in this embodiment is only about 3 days, which is shorter than the conventional coating method. The coating methods of the present application also increases the coated surface area of the bone particle by an average of 1300% as described in Example 1.

In some embodiments, a coated porous ceramic granule having an increased surface area is provided, the porous ceramic granule comprising hydroxyapatite in an amount of about 8 to about 22 wt. % and beta-tricalcium phosphate in an amount of about 78 to about 92 wt. %. The porous ceramic granule having micropores having an average diameter of about 50 μm to about 800 μm, and each porous ceramic granule having an average particle size of about 0.25 mm to 2.0 mm, the porous ceramic granule having a mineral coating thereon, the mineral coating comprising nanostructures having an average size range from about 5 to about 500 nanometers, wherein the porous ceramic granule has a BET surface area from about 0.4 to about 9.5 $m^2/g$.

In some embodiments, there is a coated bone particle provided that is made by a process of providing a first mesh having a first set of openings to allow coating liquid and bone particles of a select size therethrough and bone particles larger than the select size to remain on the first mesh; adding bone particles to the first mesh; and contacting the bone particles with the coating liquid so as to allow bone particles larger than the first set of openings to remain on the first mesh and bone particles smaller than the first set of openings and the coating liquid to pass therethrough so as to coat bone particles at least on the first mesh.

In some embodiments, a porous ceramic granule is provided, the porous ceramic granule coated with a mineral coating comprising nanostructures having an average size range from about to about 500 nanometers, wherein the coated porous ceramic granule has a BET surface area from about 0.1 to about 9.5 $m^2/g$.

Meshes

In various embodiments, at least two meshes are used to coat the bone particles. The meshes and the optional housing(s) can be made of the same or different material. In some embodiments, the meshes and the optional housing(s) can comprise material that will not degrade or corrode in the coating liquid. In some embodiments, the mesh and the optional housing(s) can comprise a corrosion resistant metal or plastic. In some embodiments, the mesh and the optional housing(s) can comprise the same or different material from each another.

In some embodiments, the mesh and the optional housing(s) can comprise a polymer including acrylic resin, alginate, caprolactone, collagen, chitosan, hyaluronic acid, hydrogel, hydroxybutyric acid, nylon, polyanhydride, polycaprolactone (PCL), poly(dimethylglycolic acid), polydioxanone (PDO), polyester, polyethylene, poly(ethylene glycol), poly(glycolide) (PGA), poly(glycolic acid), polyhydroxobutyrate, poly(2-hydroxyethyl-methacrylate), poly-lactide-co-glycolide (PLCG), poly(D,L-lactide-co-glycolide) (PLG), poly(lactide-co-glycolic acid) (PLGA), poly-lactide (PLA), polylactic acid (PLLA), poly-lactide-co-glycolide (PLCG), poly(methylethylglycolic acid), polymethylmethacrylate, polyphosphazenes, polyphosphoesters, polypropylene, poly(propylene fumarate), polyure-thane (PU), or silicone rubber, or combinations or copoly-mers thereof.

In some embodiments, the mesh can be fabricated using nonwoven techniques, such as needle punching, stitch, ther-mal or chemical bonding, hydro entanglement, felted or point-bonded, or with additive manufacturing methods (e.g., 3D printing). The mesh has a pore size that is large enough to allow small bone particles to pass through while retaining large bone particles.

The meshes are stackable. In some embodiments, the stackable meshes are formed into a U-shape such that each layer of the stackable mesh can stack on top of each other without a separate housing. The stackable meshes are spaced apart where the distance between the bottom portion of the first mesh and the bottom portion of the second mesh ranges from about 0.5, 0.75, 1, 1.25, 1.5, 1.75, 2, 2.25 to about 2.5 inches. In some embodiments, the stackable meshes have a length ranging from about 1, 1.5, 2, 2.5, 3, 3.5, 4, 4.5 to about 5 inches. In some embodiments, the stackable meshes have a ratio of the diameter to the distance between two stackable meshes. This ratio ranges from about 1:1, 1.5:1, 2:1, 2.5:1 to about 3:1. In some embodiments the stackable meshes comprise a depth extending from the topmost of the top portion of the stackable mesh to the bottommost of the bottom portion of the stackable mesh. The depth ranges from about 0.25, 0.5, 0.75, 1, 1.25 to about 2.5 inches.

In various embodiments, the mesh is made from woven threads. The threads of the mesh can have a predetermined thickness of about 0.01 mm to about 2.0 mm, about 0.05 mm to about 1.0 mm, or about 0.1 mm to about 0.5 mm. The thickness of the threads may be uniform along the length of each thread or varied across the length of each thread. In some embodiments, some threads have a greater thickness than other threads. The threads may be sized to allow for customizable openings or pore sizes between the threads. In some embodiments, the mesh is a fully customizable mesh that can be adjusted in both length and diameter to be sized according to the needs of volume of bone particles to be coated. For example, in some embodiments, the mesh includes a length or width between about 0.1 cm to about 24 cm. In some embodiments, the mesh includes a length or width of about 0.1 cm, 0.2, 0.3, 0.35, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, or 24 cm.

The mesh can be a porous mesh such that the coating liquid and certain sized bone particles may pass through the openings of the mesh. The porous mesh can have openings or pore sizes of from about 50 microns to about 1000 microns to capture different size bone particles and let others through the openings to the other meshes. In some embodi-ments, the openings of the mesh can be about 50, 80, 100, 120, 150, 180, 200, 220, 250, 280, 300, 350, 400, 450, 500, 550, 600, 650, 700, 750, 800, 850, 900, 950 to about 1000 microns. Generally, the openings of the mesh vary depend-ing on the desired distribution of the bone particles in each layer of the stackable meshes. In some embodiments, when the bone particles comprise 100 to 300 microns, the first layer of stackable mesh (e.g., the first mesh) may have openings of 255 microns, the second layer of stackable mesh (e.g., the second mesh) may have openings of 212 microns and the third layer of stackable mesh (e.g., the third mesh) may have openings of 160 microns.

When the bone particles have a similar distribution of different sizes, then the bone particles are equally distributed in each layer of stackable mesh to maximize the contact area between the bone particle and coating liquid. When the distribution is concentrated at a certain layer of stackable mesh, the bone particles may agglomerate together and decrease the contact surface area between the bone particle and coating liquid. In some embodiments, the mesh may have various shapes including disc, cylindrical, square, or rectangular shapes.

Methods of Use

In various embodiments, the coated bone particles are used to form an implantable bone implant or an implantable composition that can be implanted into the bone defect. The bone implant with the coated bone particles now has increased surface area that is beneficial for hydration of the implant and bone remodeling. In some embodiments, the bone implant includes one or more channels (which are recesses) which not only serve as surface markers but also increase the surface area and hydration characteristics of bone implant. Channels are recesses that can have a macro half-cylindrical shape, or other shapes, for example, disc shape, a trapezoidal shape or square shape, which can be easily identifiable under visible light.

In various embodiments, the plurality of coated bone particles may be mixed with already existing bone products such as bone strips, putty and pastes. Such bone products may include, but are not limited to, MasterGraft® Strips produced by Medtronic Sofamor Danek, Inc., Memphis, Tenn.; MasterGraft® Putty produced by Medtronic Sofamor Danek, Inc., Memphis, Tenn., and/or Matrix EXT compres-sion resistant products produced by Medtronic Sofamor Danek, Inc., Memphis, Tenn.

In various embodiments, a method of treating a bone defect is provided. The method comprises implanting a bone implant into the defect, the bone implant comprising a porous ceramic granule comprising hydroxyapatite in an amount of about 8 to about 22 wt. % and beta-tricalcium phosphate in an amount of about 78 to about 92 wt. %, the porous ceramic granule having micropores having an aver-age diameter of about 50 μm to about 800 μm, and each porous ceramic granule having an average particle size of about 0.1 mm to 2.0 mm, the porous ceramic granule having a mineral coating thereon, the mineral coating comprising nanostructures having an average size range from about 5 to about 500 nanometers, wherein the porous ceramic granule has a BET surface area from about 0.4 to about 9.5 m²/g.

In some embodiments, the coated bone particle can have a BET surface area from about 0.1, 0.2, 0.3, 0.4, 0.5, 0.6, 0.7, 0.8, 0.9, 1.0, 1.5, 2.0, 2.5, 3.0, 3.5, 4.0, 4.5. 5.0, 5.5, 6.0, 6.5, 7.0, 7.5, 8.0, 8.5, 9.0 to about 9.5 m²/g. In some embodi-ments, the porous ceramic granules before coating can have a BET surface area from about 0.1, 0.2, 0.3, 0.4 to about 0.5 m²/g.

In some embodiments, the bone implant containing the mineral coating can be hydrated with fluid comprising bone marrow aspirate, saline, sterile water, blood for injection, phosphate buffered saline, dextrose, Ringer's lactated solu-tion, or a combination thereof before, during or after the bone implant is implanted into the bone defect. The ratio of fluid to the coated bone particles can be from about 0.5:1 to about 3:1. In some embodiments, the ratio of fluid to the coated bone particles can be from about 0.5:1, 0.6:1, 0.7:1, 0.8:1, 0.9:1, 1:1, 1.1:1, 1.2:1, 1.3:1, 1.4:1, 1.5:1, 1.6:1, 1.7:1, 1.8:1, 1.9:1, 2:1, 2.1:1, 2.2:1, 2.3:1, 2.4:1, 2.5:1, 2.6:1, 2.7:1, 2.8:1, 2.9:1 to about 3:1.

In some embodiments, the hydrated coated bone particles can have a flowable viscosity starting from about 50 Pascal-second (Pa-s), 100 Pa-s, 150 Pa-s, 200 Pa-s, 250 Pa-s, to about 300 Pa-s and reaches a higher viscosity from about 500 Pa-s, 750 Pa-s, 1000 Pa-s, 1,500 Pa-s, 2,000 Pa-s, 2,500

Pa-s to about 3,000 Pa-s. In some embodiments, the hydrated bone particles can have a flowable viscosity starting from about 50 Pa-s to about 3,000 Pa-s and reach a higher viscosity from about 3,000 Pa-s to about 300,000 Pa-s.

The coated bone particles can have a certain density when hydrated. For example, when the coated bone particles are hydrated, the density can be from about 1.2 to about 2.0 g/cc or from about 1.4 to about 1.6 g/cc. In some embodiments, the hydrated bone particles can have a density from about 1.2, 1.3, 1.4, 1.5, 1.6, 1.7, 1.8, 1.9 to about 2.0 g/cc.

The coated bone particles, once hydrated and placed into an implant can have a modulus of elasticity from about 2 MPa to about 12 MPa, such as from about 2, 3, 4, 5, 6, 7, 8, 9, 10, 11 to about 12 MPa.

Having now generally described the invention, the same may be more readily understood through the following reference to the following example, which is provided by way of illustration and is not intended to limit the present invention unless specified.

Example 1

Figure 5:
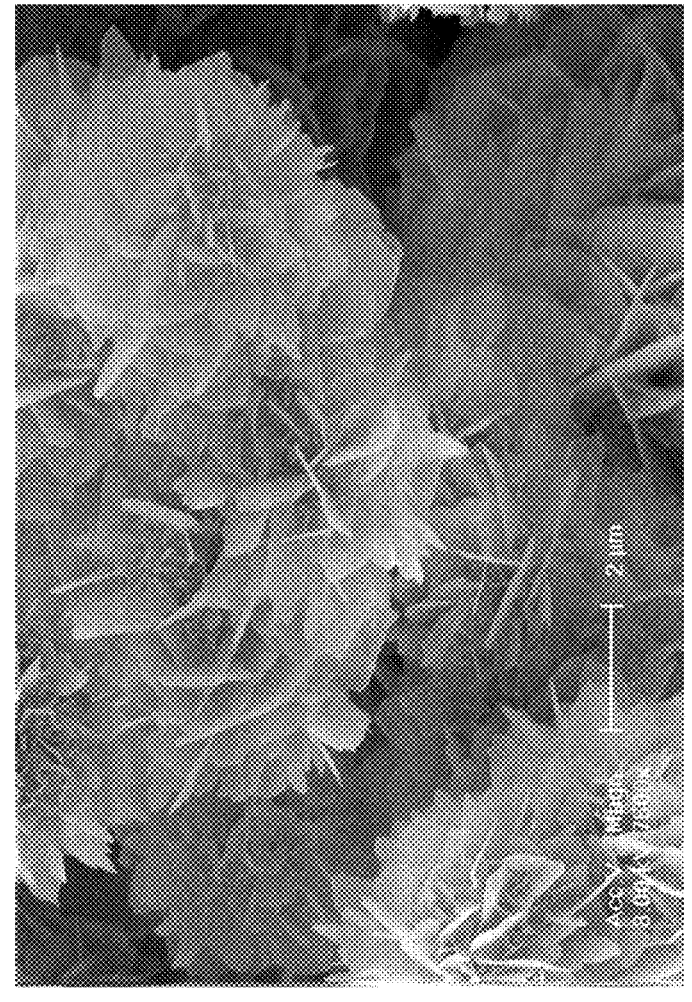
FIG. 5 is a scanning electron micrograph (SEM) of coated bone particles with a mineralized nano-apatite coating.

Example 1 is directed to the method of coating bone particles. Autografts are the gold standard for bone grafting but the supply and use of autografts is limited by donor site morbidity and sub-optimal bone quality in some patients. Consequently, synthetic bone graft substitutes are increasingly being used in clinical settings although none of them are as effective as autografts. Therefore, we developed a Nano-Apatite coating, as shown in FIG. 5, that is grown onto implant surfaces, and this results in performance characteristics, for the implant, that approach that of the autograft model. The coating is a bone mineral that is grown under physiological conditions through a biomimetic process. This coating has a plate-like nanostructure, which is semi crystalline and non-stoichiometric. The nanotopography is known to promote osteoblast adhesion and enhanced osteoblast function by sensitively regulating the protein interactions that lead to cell attachment, differentiation and proliferation.

However, coating a large number of micron-sized MasterGraft® granules is a challenge. This is because the interactions between the granules during a normal coating process impacts the quality of the nanotopography. We show an improved method of growing a nano-apatite coating on these challenging substrates using micron-sized (90-600 μm) MasterGraft® granules, synthetic biphasic calcium phosphate, as an example. The coated bone particles in accordance with the methods and apparatus provided here have macropores and micropores, as shown in FIG. 6.

In general, the substrates (e.g., bone particles) are first cleaned in a caustic bath, rinsed, and then immersed in a modified simulated bodily fluid (mSBF) which provides a calcium and phosphate rich environment to facilitate crystallization. The mSBF is refreshed every day for three days, and then rinsed with water and finally dried.

For a pilot scale, three sizes (255, 212 and 160 μm) of nylon mesh are utilized to suspend granular bone particles (MasterGraft®) in the modified simulated body fluid (mSBF), as shown in FIG. 1A, FIG. 1B, and FIG. 3B. A recirculating bath is used to maintain physiologic temperature as well as ensure that a controlled rate of interaction between mSBF and granules occurs throughout the coating process. The stackable meshes allow for an increased density of material within the container while maintaining mSBF flow around the granules. Once coating is complete, the meshes allow a technician to transfer product directly to an oven for drying, as shown in FIG. 4. As a result, the individual granules are prevented from interacting with each other and disrupting the growth of the nano-apatite plates. The scanning electron micrograph of the comparison of uncoated bone particles and the coated bone particles are illustrated in FIG. 7. The specific surface area (SSA) increases ranging from about 1106% to about 1840% with a mean of about 1300%, as shown in Table 1 below.

TABLE 1

| Specific surface area of coated and uncoated MasterGraft ® granules | | |
|---|---|---|
| MasterGraft ® granules | Specific Surface Area (SSA: m²/g) | % increase in SSA |
| Uncoated | 0.48 | N/A |
| Coated with Nano-Apatite | 5.31-8.83 (mean = 6.24) | 1106%-1804% (mean = 1300%) |

The pilot scale to improve the coating process was successfully demonstrated. Scanning electron micrographs demonstrated that the plate-like nano topography of the coating is undamaged as compared to a coating process conducted with the substrates on the bottom of a container. Additionally, specific surface area of the coated granules was increased on average by 1300% as measured by BET.

Although the invention has been described with reference to preferred embodiments, persons skilled in the art will recognize that changes may be made in form and detail without departing from the spirit and scope of the invention.

What is claimed is:

1. A plurality of coated porous ceramic granules comprising:

porous ceramic granules comprising hydroxyapatite in an amount of about 8 to about 22 wt. % and beta-tricalcium phosphate in an amount of about 78 to about 92 wt. %, the porous ceramic granules having micropores having an average diameter of about 50 to about 800 μm, and the porous ceramic granules having an average particle size of about 0.1 to 2.0 mm;

a mineral coating on each of the porous ceramic granules, the mineral coating being about 97 wt. % hydroxyapatite and about 3 wt. % octacalcium phosphate, comprising plate-like nano-apatite structures having an average size range from about 100 to about 200 nm, and having a porosity between about 20 and about 28 wt. %;

wherein the coated porous ceramic granule has a BET surface area from about 5 to about 10 m²/g, wherein the mineral coating has a thickness from about 1 to about 200 nm, and is uniformly formed on the entire surface of each porous ceramic granule such that the coated porous ceramic granules have a larger BET surface area that is from about 1106% to about 1840% of that of the porous ceramic granules without the mineral coating.

2. A method of coating porous ceramic granules according to claim 1, the method comprising:

providing a first mesh having a first set of openings to allow coating liquid and porous ceramic granules of a select size therethrough and porous ceramic granules larger than the select size to remain on the first mesh;

adding porous ceramic granules to the first mesh; and contacting the porous ceramic granules with the coating liquid so as to allow porous ceramic granules larger than the first set of openings to remain on the first mesh and porous ceramic granules smaller than the first set of openings and the coating liquid to pass therethrough so as to coat porous ceramic granules at least on the first mesh;

wherein the coated porous ceramic granules of claim 1 are formed.

3. The method of claim 2, wherein the method comprises providing a second mesh having a second set of openings to allow the coating liquid and porous ceramic granules of a select size therethrough and porous ceramic granules larger than a select size to remain on the second mesh, the second set of openings of the second mesh being smaller in size than the first set of openings of the first mesh, the second mesh having a top portion, and the first mesh having a bottom portion, the bottom portion of the first mesh being stacked above the top portion of the second mesh so as to allow the coating liquid to pass through to the second mesh so as to coat the porous ceramic granules at least on the second mesh.

4. The method of claim 3, wherein the contacting comprises adding the coating liquid to suspend the porous ceramic granules on the first mesh or on the second mesh or on both the first mesh and second mesh.

5. The method of claim 3, wherein the contacting comprises immersing the first mesh and the second mesh in the coating liquid to suspend the porous ceramic granules on the first mesh or second mesh or on both the first mesh and second mesh.

6. The method of claim 5, wherein the immersing of the first mesh and the second mesh occurs in a container filled with the coating liquid.

7. The method of claim 2, wherein the coating liquid is added to a fill line forming a bath and the porous ceramic granules are below that fill line.

8. The method of claim 3, wherein the second set of openings allows the coating liquid and porous ceramic granules smaller than the select size therethrough to a housing or container configured to hold the mesh and hold any remaining coating liquid.

9. The method of claim 8, wherein the housing or the container has an outlet configured to be coupled to a pump to replenish coating liquid.

10. The method of claim 2, wherein the coating liquid contacting the porous ceramic granules forms a surface coating on the porous ceramic granules.

11. The method of claim 3, further comprising drying the porous ceramic granules remaining on the first mesh, or second mesh, or on both the first mesh and the second mesh in an oven.

12. The method of claim 3, wherein method further comprises stacking at least a third mesh, a fourth mesh, a fifth mesh, or a sixth mesh below a bottom of the second mesh.

13. The method of claim 2, wherein the method further comprises providing an additional mesh having a set of openings having the same size as the openings of the first mesh, and contacting the additional mesh with the coating liquid and porous ceramic granules.

14. The method of claim 2, wherein the first mesh is only one single mesh.

* * * * *